United States Patent [19]

Molin et al.

[11] Patent Number: 5,173,418
[45] Date of Patent: Dec. 22, 1992

[54] PRODUCTION IN *ESCHERICHIA COLI* OF EXTRACELLULAR SERRATIA SPP. HYDROLASES

[75] Inventors: Soren Molin, Holte; Michael Givskov; Erik Riise, both of Copenhagen, all of Denmark

[73] Assignee: Benzon Pharma, A/S, Hvidovre, Denmark

[21] Appl. No.: 476,960

[22] Filed: Feb. 7, 1990

Related U.S. Application Data

[62] Division of Ser. No. 372,679, Jun. 28, 1989, abandoned, which is a division of Ser. No. 20,943, Jan. 8, 1987, abandoned.

[30] Foreign Application Priority Data

May 10, 1985 [DK] Denmark ............................ 2100/85
Dec. 23, 1985 [DK] Denmark ............................ 6060/85

[51] Int. Cl.⁵ .......................... C12N 9/20; C12N 9/22; C12N 15/55
[52] U.S. Cl. .................................... 435/198; 435/199; 536/27
[58] Field of Search ...................... 435/69.1, 72, 252.33

[56] References Cited

U.S. PATENT DOCUMENTS

| | | | |
|---|---|---|---|
| 3,960,659 | 6/1976 | Fazakerley | 435/270 |
| 4,039,382 | 8/2977 | Thang et al. | 435/175 |
| 4,161,424 | 7/1979 | Ando et al. | 435/199 |
| 4,495,287 | 1/1985 | Uhlin et al. | 435/231 |
| 4,499,189 | 2/1985 | Uhlin et al. | 435/252.33 |
| 4,614,718 | 9/1986 | Seino et al. | 435/72 |

FOREIGN PATENT DOCUMENTS

| | | |
|---|---|---|
| 0095361 | 5/1983 | European Pat. Off. . |
| 0109150 | 3/1984 | European Pat. Off. . |
| 0123903 | 3/1984 | European Pat. Off. . |
| 0131418 | 6/1984 | European Pat. Off. . |
| 0146929 | 12/1984 | European Pat. Off. . |
| 3334847 | 4/1985 | Fed. Rep. of Germany . |

OTHER PUBLICATIONS

Gunner S. Skogman et al. Factors Affecting the Biosynthesis of L-Tryptophan by Genetically Modified Strains of *Escherichia coli*, Journal of General Microbiology 130:3091–3100 (1984).
Chemical Abstracts 103: 19095b (USSR Pat. No. 1,146,321).
Chemical Abstracts 92: 176305s (Severina et al.).
Chemical Abstracts 96: 213050k (Roy).
Jacobs et al., Nature 313: 806–810, (1985).
Vasil et al. *J. Bacteriol.* 152: 431–440 (1982).
Pierre Cornelis et al., Cloning and Expression of a *Bacillus coagulans* Amylase Gene in *Escherichia coli Mol. Gen. Genet,* (1982) 186:507–511.
B. A. Cantwell et al., Molecular cloning and expression of a *Bacillus subtilis*β-glucanase gene in *Escherichia coli-Gene,* 23:211–219 (1983).
Maria Yang et al., Nucleotide sequence of the amylase gene from *Bacillus subtilis, Nucleic Acid Research,* 11:237 (1983).
Legakes, et al., Chem. Abstract vol. 90, 18831q.
BRL Catalog, 1985, p. 25.
Isolation and Properties of an Exocellular Nuclease of *Serratia marcescens* Eaves et al., J. Bateriol., pp. 273–278, Jul. 20, 1962.
Chem. Abstracts, vol. 103 No. 66030.

(List continued on next page.)

Primary Examiner—Richard A. Schwartz
Assistant Examiner—James Ketter
Attorney, Agent, or Firm—Iver P. Cooper

[57] ABSTRACT

Extracellular Serratia spp. enzymes have been found to be excreted by another gram-negative organism harbouring a plasmid carrying DNA from Serratia spp. encoding the enzymes. This organism, e.g. *E. coli,* is therefore employed to produce the enzymes, specific examples of Serratia spp. enzymes produced are a nuclease, a lipase and a phospholipase. The nuclease may be employed to remove nucleic acids from a biological material.

10 Claims, 13 Drawing Sheets

OTHER PUBLICATIONS

"A Rapid Alkaline Extraction Method for the Osolation of Plasmid DNA" Methods in Enzymology, vol. 100, pp. 243-255.

Clegg et al. FEMS Microbiology Letters 1985, 27(3) pp. 257-262.

Emerick et al., Biotechnology, Feb. 84, V2, N2 pp. 165-168.

Journ. of Bacteriology, Jun. 1984, Dauenhauer et al., "Cloning and Expression in *Escherichia coli* of *Serratia marseens* . . . ", pp. 1128-1132.

Chemical abstract, vol. 99 (1983) abstract No. 18517 c.

J. Biochem (Tokyo), 1983, 93, pp. 1287-1295 (Eng).

Maniatis, Molecular Cloning, 1982.

G. Bertani, J. Bact. 62, 1951, p. 293.

Clark, et al, J. Mol. Biol. 23, 1967, p. 99.

Maxam et al., Proc. Natl. Acad. Sci USA 74, 1977, pp. 560-564.

Sanger et al., Proc. Nat. Acad. Sci. USA 74, pp. 5463-5467.

J. Messing, Nucl. Acids, Res. 9, 1981, pp. 390-321.

Shine, Dalgarno, Nature 254, 1975, p. 34.

R. Simon, Biol. Technology, Nov. 1983, pp. 784-791.

U. Winkler, Molec. gen. Genet. 124, 1973, pp. 197-206.

J. E. L. Larsen, Gene 28, 1984, pp. 45-54.

Chang & Cohen, J. Bacteriol. 134, 1978, pp. 1141-1156.

E. Remaut et al., Gene 15, 1981, pp. 81-93.

CORRESPONDING TO LINE 2   3   4   5   6   IN FIG. 4

```
1                                                  50                                                 100
GCCCCGCTGAAAGTCGTCTTGAAGGTGCTGCTGTGTCTTCCGGTGACGAAGATAGTCAAAGTCGCAGATCGAGCAGGAAATCGCCCAGATCG
CGGGGCGACTTTCAGCAGAACTTCCACGACGACAGAAGCCACCTGTTCTATCAGTTTCACGTCTTAGCGTGTTCCAGCTCGTCTTTAGCGGGTCTAGC 101                                                150                                                200
AACAGGCGGTGTGCGCCCGGGGGGCTCCGGTATCACCGGGTACGGCAGATGACGGCATTACGTTCGCCCACGGTCAACGACCTCTGCTGATAATC
TTGTCCGCCACACGCGGGGCCCCCGAGGCCATAGTGGCCGCATACTGCCGTAATGCAAGCGGGTGCCAGTTGCTGACGACCTATTAG 201                                                250                                                300
CCCCCTTTGAAACGGGCGTCTGTTGGACGGGCTTTATTTCCCGCCGCATTCACGTGCGGGTGCCTGTACCATGACTGACACATTCACAACATGAATATGTT
GGGGGAAACTTTGCCCGCAGACAACCTGCCGCGTAAAGGGCGGCGTAAGTGCACGCCCACCGGACATGGTACTGACTGTGTAAGTGTTGTACTTATACAA 301                                                350                                                400
GCATTGTTCTATTCGTTCACTGCCATAAGTTTAATTTACTGTAAATATACAGTACTTTTTTAACTTATTGAGGATATGAATATGGCTTTAACAAC
CGTAACAACATAAGCAACGTGACGCTATTCAAATTAAATGACATTTATATATGTCAGAAAAAATTGAATAACTCCTATACTTATACGCGAAATTGTTG 401                                                450                                                500
AAGATGTTGGCCTTGCTGCCCCTGTCGCCCCCCCCTGTTCCGCCCACAGCCGTCGAATCCATCGGAATCGACAACTCGCGGGTCGGCTGCCCGACCGGGCA
TTCTACAACCGGAACCAGCGGACGAACAAGCGGGTTGCCGCAAGCGGGTTAGTAGCTGGTGCCTCAAGCCGGAGTTGAGCGGCAGGCTGCCCGCCGT 501                                                550                                                600
GCAGCAACGTGTCTATCGTGCCTCATCCTGCCTCATGCCTATACGTTGAACAACAACAGGCACCACCAAGTTCGCCAACTGCCAACTGGGTGCCTTATCACATCACCAAAGACACACC
CGTCGTTCCACAGATAGCCACCCAGTACCACCGAATATGCAACTTGTTGTGTTGTTGCCCACCGGTTGACCGGGGTTGAAGCGGGTTGCCACCGAATAGTGTAGTGTTTCTGTGTGG 601                                                650                                                700
GGCCAGCGGGCAAGACGCGCAACTGCGAAACCGATCCGCTCAACCCCGGCCGCGATTACACTCGCCCCAACGCGGCCGGGCCTGAAG
CCGGTCGCCCGTTCTCGCCGTTGACCTTTGCCCTTGGCTAGGCCGCCGGAGTTGGGCCGCTAGGCCAATGTGAACCGGCCGGTTGACCGGCCGTTGCCCGGCCGACTTC
```

Fig. 7a.

```
 701 GTCGATCGCGGTCATCAGGCGGCGCCTTGGCCTCGCTGGCCGGGCTCCGACTGGGAATGCCTGAATTACCTGTCCAACATCACGCCCGCAAAGTCCGATC  800
     CAGCTAGCGCCCAGTAGTCCGCGGCGACCCGACCCCCCGACGAGCGACTGACCCTTAGCGACTTAATGACAGTTGTAGTGCGGCGTTTTCAGGCTAG
 801 TTAACCAGGCGGGCTCGGGCCGGCCCCCCCTGGGCCCTCGAAGATCACGAACGCAAGCTGATCGCCCGATATCCTCGGTCTATACCGTGACCGGGCCGCTGTATGA  900
     AATTGGTCCCCGGGACCCGGCCGGGCCGACCTTCGTTCGGCTTCCTTGCGTTCGACTAGCTAGCGGGCCTATAGAGGACCAGATATGCCACTGGCCCCGGACATACT
 901 ACCGGATATGGCGCAAACTGCCCGGCACCCCAGAAAGCCGCACACCATCCCCAGCCGCCCCTACTGCAAGCTGATTTTCATCAACAACAGCCCGGGTGAACCAC  1000
     TGGCCTATACCCGTTTGACCGGCCCGTTGGGTCTTTGCGGTCGTGTGTAGGGTCCGGATGACCTTCGACTAAAGTAGTTGTTGTCGGGGCCCACTTGGTG
1001 TATGCCCGCTTCCTGTTCGATCAGAACACCCCGAAGCGCCCGATTTCTGCCAATTCCGCGTGACGTGACGATCGAGAAACGCACCGGCCTGATCA  1100
     ATACGGGCGAAAGGACAAGCTAGTCTTGTGCGGCTTCCCGGCGCTAAGAGCGGTTAAGGCGCACTGCCACTCGTCTAGCTCTTGCTGCCGGACTAGT
1101 TCTGGGCCGGTGTCCGGACGAGCTCCGCTCCAGGCTTCCGCTCCAAGAGCAAACCGGCCTCTCGCCGGAGTTGATGGGCTGCAAAAACTGACGAAAACGCCGAAG  1200
     AGACCCGGGCCAGAGCCTCGTCCGAAGCGACTCCGACGACTTCTCGTTTGCGCCGGACGACGCCCTCAACTACCACGCGAGCGTTTTTGACTGCTTTTGGCGGCCTTC
1201 CGGGTTTATTTTTCACCGGCGGCGGCGGCGATTATCCCGTCGCGCCTTTGCGGCCCTTCGGGGCGCCAACTCACGCTGAGGGGTGAGGCTACCGGGGCC  1294
     GCCCAAATAAAAAGTGCCGCCGCCGCCGCCGCTAATAGGGCACGCCCGGGAAAACGCCGGCGAGCTGACGACTGCGACTCCGATGGCCCGG
```

Fig. 7b.

```
                                                                                           300
201  GTTATCGCCCCGCCACCTTTACCGAAAGCCTGTAATTTCGCGGCCAGTCAATCAGGAGCTTCGGCTCCCTTTCTCGGCGTTTGGGCGGCCGAAAACCGAACGTG
     CAATAGCGGGCGGTGAAATGGCTTTCGGACATTAAACGCCGGCCGTCAGTTAGTCCTCGAAGCCGAGGGAAGACCGCAAACCGCGGCTTTGGCTTTGCAC
```

CAP-SITE, PROMOTER AREA.

```
                                                                                           400
301  GATCACATTCTGTACAAAGATAAGCATTCTAATACAGAACTCATCGCCGACTTGCCGATAGCTAAATCAGCACCTATTTAGTCTCAATAAAAGTCTAT
     CTAGTGTAAGACATGTTTCTATTCGTAAGATTATGTCTTGAGTAGCTGAAACGGCTATCGATTTAGTCGTGGATAAATCACGAGTTATTTTCAGATA
              S.D.        phl-gene →           .PstI   450
```

```
                                                                                           500
401  CGACAAGGAGTCGCATCAGTATCCCTTTAAGTTTTACCTCTCCAGTATCCCCGGTGGCCGCGATCCCCTACGCCTCGCGCCGCTGCCGAGACGCGGACGG
     GCTGTTCCTCAGCCGTAGTCATACGGAATTCAAAATGGAGACGTCATAGGGGCCACCGGCGCGCTAGGACGCGGCGACGGCTCTGCGCCTGCC
     fMETSerMETProLeuSerPHETHRSERALAValSERPROVALALAALAILEProThrProARGALAALAALAGLuThrargThrA
```

EcoRV

```
                                                                                           550
501  CGGGGAGCCTGCGGCCACCGACGCCCCCGGCAAATCCGGGCCGTGCCCCTCGGCCCCTCTCAGAACGCCTGAACGCCGAGAATCTGTTGAATACCGCTCGGTCGCCGATAT
     GCCCCTCGGACGCCGCTGGGGCGCCGGGCCCGTTTGCCGACCTTGCGGCGCTCTTGCGACTTGCCACTTATGCCGACCAGCCGCTATA
     LAALASerLEUargHisALAGLYLYSSERglyPROVALALASERProSERGLNASNThrLEUASNALAGLNAsnLEULeuAsnThrLEUValGLYASPIL
```

Fig. 9a.

```
601 CTCAGGGCGGCGACCGACGGGCGGGGCGAGGCCCGGGCGGTGACGCGGGCGTGACGCGGCAATCGCAGGAGGGGATTATGCTTGGCCTGTTGCCAAGGACGTT
    GAGTCGCCGCCGCTGGCTGCCGCGTCCGGCGTCCGGCACTGCCCCCGTCGTTAGCGTCCTCCCCCGTCCTAATACGCGACAACCGGTTCCTGCAA
    ESerALAaLAaLaPROThrALAaLAaLaALAPROGLYVALThrargglyGLNGlnSerGLNGluglyASPTYrALALeuALALeuALALysASPVAL
                                                                                                                    700

701 TACTCACTCAATGGCCAGGGCGCCCGGGTTCAACCCCCTGAGCGACAGCCCCTCCTCCGGTTTCGGCATCGATCCCCCACCCTGCACGACGGGGCA
    ATGAGTGAGTTACCGGTCCCGCGGCGCCAAGTTGGGGGACTCGCTGTCGGCCGGAGCCAAAGCCTAGCTAGGCGCGTCCGACTCCGCTCTGCGCCCGT
    TYRSerLeuAsnGLYGLnGLYALAaLaAlaglyPHEasnARGLEUSerASPSerALALEULeuGLYPHEGLYILEASPProALASerLEUHisASPALAGLYS
                                                                                                                    800

801 GCGGTTTCCAGGCTGGGATTTACAGCAACGACAAACAGTATGTCTTGCCGCTTCGCCCTGCACCAACGACTGCCTGCTGAGCAACGTGCGGCAGGC
    CGCCAAAGGTCCGACCCTAAATGTCGTTGCTGTACACAACGGCCGAAGCGGCGTGGTTGCTAACCGCGTAACGACTCGTTGCACGCCGTCCG
    erGLYPHEGLNALAglyILETYRSerASNASPLYSGLnTYRVALLeuALAPHEaLAGLYTHRasnaSPTrPARGaSPTRPLEUSerASNVALargGLNAL
                                                                                                                    900
```

1301
ACGGCGCCACGGCATCGACAAGGTGATAAGCTCGATGGCGGAACAAAAGCCGTGGAGCCGGAAGGCCAATGCCTGAAGGGGCGTCGCTTGCGGGGGCTG
TGCCCGGTCCCGTAGCTGTTCCACTATTCGAGCTACCCCTTGTTTCGGCACCCTCCGTTCCCGTTACGGACTTCCCCAGCGAACGCCCCCCGGAC
ThrALAHisGLYIleSerSerMETALAGLUGlnLysPROTRPGluALALysALAAsnALA.
                                                    1350 phl-stop                                           1400

1401
GCGATAGCCTTACTGGCCTGCTCGCCGGTGACCGGTTTACTGAGGCTAAGGAGCAACAGATGGGCAGGAGATTTCGCCGTTTGACGGCCACAGCG
CGCTATCGGAATGACCCGGACGGCCACTGCCCAAATGACTACTACCGATTCCTCGTGTCTACCCCGTCCTCTAAAGCGGCAAACTGCCGGTGTCGC
                                                    1450                                                    1500

1501
AATCTGCCCTGCCTCAGCGCCTCAGGCGGTGGGCCGGTGGGCGATACGGCAGGTATCCATGCCAGCCACCGAGGATCGCTTCCGCGAACGGGCGATCGGCAGGTCA
TTAGACCCGACGGAGTCGCGCCAGCCGGTCCCGCCACCCGGCTATGCCGTCCCATAGGTACGGTCGTCCGGTCCTGGCGTGCGTTGCCCCGGTAGCCGTCCAGT
                    1550FspI                                                 1600

Fig. 9d.

PRODUCTION IN *ESCHERICHIA COLI* OF EXTRACELLULAR SERRATIA SPP. HYDROLASES

This is a divisional of U.S. application Ser. No. 07/372,679, now abandoned, filed Jun. 28, 1989, which is a divisional of U.S. application Ser. No. 07/020,943, filed Jan. 8, 1987, now abandoned.

The present invention relates to a method of producing bacterial enzymes and to hybrid plasmids and microorganisms useful in the method. The invention further relates to the use of one of the enzymes, nuclease, for removing nucleic acids from a biological material, as well as to a regulatory region useful for initiating gene expression.

Serratia spp. have been found to produce a number of hydrolytic enzymes which are excreted into the culture medium. This is in contrast to other gram-negative bacteria, in which proteins are preferentially excreted to the periplasmic space rather than to the surrounding medium. Such periplasmic proteins tend to leak into the culture medium, especially when the cells are grown to high densities.

According to the present invention, DNA encoding extracellular Serratia spp. enzymes (that is, extracellular when expressed in Serratia), has been isolated, and microorganisms suited for the industrial production of gene products and harbouring the Serratia DNA have been grown and have been found to produce the Serratia enzymes.

It was also found that when hybrid plasmids containing inserted DNA encoding an extracellular Serratia spp. enzyme were harboured by another microorganism which, in itself, does not usually excrete its gene products into the culture medium, i.e. *E. coli*, the Serratia enzyme was, to some extent, excreted by *E. coli* into the culture medium (cf. Examples 1 and 6). It is therefore possible to partially purify the portion of the Serratia enzyme excreted into the culture medium from the *E. coli* cells in a relatively simple way, for instance by filtration to remove the *E. coli* cells, and precipitation of the enzymes from the filtrate, for instance with ammonium sulphate. In the present context, the term "excrete" is understood to mean transport of a gene product through at least the cytoplasmic membrane of the cell.

Thus, one aspect of the invention relates to a method of producing a bacterial enzyme, comprising cultivating, in a culture medium, a microorganism harbouring a hybrid plasmid which contains DNA from Serratia spp. encoding an extracellular Serratia spp. enzyme, and harvesting the enzyme from the culture.

In a particular embodiment, the invention relates to a method for producing Serratia spp. enzymes substantially free from other bacterial proteins, in which a portion of the enzyme is excreted from the microorganism into the culture medium and harvested from the culture medium.

The cultivation of the microorganism is preferably performed in a liquid culture medium containing the nutrients and minerals required for the optimal growth of the microorganism. The harvesting of the enzyme may be performed in a manner known per se. As mentioned above, the purification of the enzyme may be performed by filtration to remove the host cells, and precipitation of the nuclease from the filtrate. Normally, the precipitate is then dissolved in a suitable buffer, e.g. Tris-EDTA, followed by dialysis to remove the precipitation agent.

Examples of hydrolytic enzymes produced by Serratia spp. are a nuclease which hydrolyzes nucleic acids into nucleotides, oligonucleotides, or smaller nucleic acid fragments, and a lipase and a phospholipase which hydrolyze fatty acids from lipids and phospholipids.

The microorganism is typically a bacterium, preferably a gram-negative bacterium. It is normally not desirable to employ Serratia spp. for the production of the Serratia spp. enzymes, as Serratia spp. are opportunistic pathogenic bacteria, which may limit their utility as production microorganisms. Furthermore, Serratia spp. produce an extracellular protease which may contaminate the desired product. The preferred gram-negative bacteria for use as production microorganisms for the production of the Serratia spp. enzymes are bacteria generally employed for the production of gene products such as *E. coli*.

The invention also relates to a hybrid plasmid which carries DNA from Serratia spp., encoding an extracellular Serratia spp. enzyme as described above.

Plasmids useful as vectors for the production of the enzymes according to the invention may be any type of plasmid usually employed for this purpose which is able to replicate in the microorganism in question. Plasmids which may be used to produce large quantities of the enzymes in question are, e.g., the so-called runaway plasmids, that is, plasmids with a conditionally uncontrolled replication behaviour. Plasmids showing this behaviour are disclosed, in, for instance, U.S. Pat. No. 4,495,287 and European Patent Application, Publication No. 0109150.

Bacterial nucleases are enzymes which are of considerable value in the purification of, e.g., proteinaceous products prepared by the fermentation of microorganisms such as products prepared by the fermentation of cells modified by recombinant DNA techniques and producing products not naturally associated with the cell in question. An important step in the purification of these products is to separate the proteinaceous products from nucleic acid derived from the cells. This purification, when performed by standard chemical treatments such as precipitation of the nucleic acids, incurs a risk of loss of the desired product produced by the cells due to the high viscosity of the material containing the desired product which renders separation thereof difficult, whereas the decomposition of the nucleic acids by means of nuclease does not incur any substantial loss of the desired product. Also, the efficient and complete removal of nucleic acids from the products is important, e.g., when the products are to be used for administration to human beings, as it is a requirement by health authorities in some countries that the product should not contain any hybridizable DNA from the cells employed to produce the product in question.

Therefore, a highly interesting enzyme produced by Serratia spp. is a nuclease which has been found to be very potent and which is of great industrial importance for the removal of nucleic acids from a biological material. In the present context, the term "removal of nucleic acids" is intended to indicate that long nucleic acid sequences are degraded to shorter fragments or oligonucleotides or, in some cases, to mono- or dinucleotides. This means that the products resulting from the nuclease action are rather easy to remove by conventional separation methods.

Accordingly, the present invention further relates to a bacterial nuclease which is a Serratia spp. nuclease with the following amino acid sequence (deduced from the DNA sequence in a manner known per se, and including the N-terminal signal peptide):

MetArgPheAsnAsnLysMetLeuAlaLeuValAlaLeuLeuPheAlaAlaGlnAlaSerAlaAsp
ThrLeuGluSerIleAspAsnCysAlaValGlycysProThrGlyGlySerSerAsnValSerIleValArg
HisAlaTyrThrLeuAsnAsnSerThrThrLysPheAlaAsnTrpValAlaTyrHisIleThrLysAsp
ThrProAlaSerGlyLysThrArgAsnTrpLysThrAspProAlaLeuAsnProAlaAspThrLeuAlaProAla
AspTyrThrGlyAlaAsnAlaAlaLeuLysValAspArgGlyHisGlnAlaProLeuAlaSerLeuAlaGly
ValSerAspTrpGluSerLeuAsnTyrLeuSerAsnIleThrProGlnLysSerAspLeuAsnGlnGlyAla
TrpAlaArgLeuGluAspGlnGluArgLysLeuIleAspArgAlaAspIleSerSerValTyrThrValThr
GlyProLeuTyrGluArgAspMetGlyLysLeuProGlyThrGlnLysAlaHisThrIleProSerAlaTyr
TrpLysValIlePheIleAsnAsnSerProAlaValAsnHisTyrAlaAlaPheLeuPheAspGlnAsnThr
ProLysGlyAlaAspPheCysGlnPheArgValThrValAspGluIleGluLysArgThrGlyLeuIleIle TrpAlaGlyLeuProAspAspValGlnAlaSerLeuLysSerLysProAlaSerCysArgSer |.

The enzyme may, for instance, be produced by the method described above.

For special applications, such as when a nuclease is to be used for removing residual nucleic acids from an otherwise substantially purified biosynthetic product (as described in further detail below), the enzyme should preferably be in substantially pure form. In order to obtain the substantially pure enzyme, a crude enzyme preparation may be partially purified by ultrafiltration or precipitation with, e.g. ammonium sulphate, and subjected to further purification by, for instance, chromatography (such as ion exchange chromatography or affinity chromatography) or preparative gel electrophoresis. In some cases, it will be an advantage to provide the enzyme in immobilized form on a suitable matrix as this may facilitate an easy removal of the nuclease after use and also makes it possible to use the enzyme once more. Examples of such matrix materials are dextran or agarose gels or an inorganic material such as a siliceous material, e.g., silica and silicic acid and derivatives thereof. The immobilization may be performed in a manner known per se.

Another enzyme of potential interest is a phospholipase produced by Serratia spp. The present invention therefore relates to a Serratia spp. phospholipase encoded by the following DNA sequence:

```
ATGAGTATGCCTTTAAGTTTTACCTCTGCAGTATCCCCGGTGGCCATCCTCGCGCCGCTGCCGAGACGCGGACGG
TACTCATACGGAAATTCAAAATGGAGACGTCATAGGGGCCACCGGCTAGGGATGCGGAGCGCGGACGGCTCTGCCGCC

CGGCGAGCCTGCGGCACGCCGGCACCGGGCCGGTGGCCTCTCCTCAGAACACGCTGAACGCGCAGAATCTGTTGAATAC
GCCGCTCGGACGCCGTGCGGGCCGTTTAGGCCCGGCCACCGGAGGAGTCTTGCGACTTGCCGTCTTAGACAACTTATG

GCTGGTCGGCGATATCTCAGCGGCGGCACCGACGGCGGCAGCGCGGGGCGTAGACGCGCAGCGCCAATCGAGGAGGGGAT
CGACCAGCCGCTATAGAGTCGCCGCGCCGTGCCTGGCTGCCGCGCCACTGCGCCCGTCGTTAGCGTCCTCCCCCCTA

TATGCGTTGGCGCTGTTGGCCAAGGACGTTTACTCACTCAATGGCCAGGGCGCCGCCGGTTCAACCGCTGAGGCACCGCTG
ATACGCAACCGGACAACCGGTTCCTGCAAATGAGTGAGTTACCGGCGGCCCAAGTTGGCGACTCGCTGTGGCGAC

CTCGGTTTCGGCATCGATCCCGCCAGCTGCACGACGGGCAGCGGTTCCCAGGCTGGGATTTACAGCAACAAACAGTAT
GAGCCAAAGCCGTAGGGCGGTCGACGTGCTGCCGCCGTCGACCCTAAATGTCGTTGCTGTTTGTCATA

GTGTTGGCGTTCGCCGGCACCAACGACTGGCTGAGCAACGTGCCGGCAGGCGACGGCTATGACGATGTGCAGTAC
CACAACCGCAAGCGGCCGTTGGTTGCTGACGGCCCGATACGTCGTTGCGATACTGCTACACGTCATG

AATCAGGCGGTTGCCGCTGCCAAAGCGCCCAAGGCGGCCTTCACCTTCAACGCGGTCATCCGGCCATTCGCTTGGTGGT
TTAGTCCGCAACGGCGACGTTTTCGGCGTTCCGCGAGCCGTGGCAGCGCCGACCACTAGCGCCGGTAAGCGAACCGACCA

CTGGCGGCCACCGGGACCGGCGAAGCGGGCATCGCGGTCACCTTCAAGCGCCGGGGTCTCGGATTACACCCTGAATCGCCT
GACCGCCGGTGGCGGCCGCTGGCCGTGGCAGCGCCAGTGGAAGTTGCGCCGCCCAGAGCCTAATGTGGGACTTAGCGGA

GGGCATCGATCCGGCGGCAGCGAAGAAAGATGCCGAAGCGGCATTCGCCGAAGCTTCGGCCGTACGCCGTTTCTAACGGCT
CCCGTAGCTAGGCCGCCGGCTGCCGCCGCCTTCTTTCTACGGCTTCGGCCGCGCTAGTGCATGTCGCTTATACTGTACGACTGGTACGT

CCCAGGAGTCGACCTGCTGCTGATCCGGATGCCATCGGCCACAACATCACCCTGGCCAACAACGATACCCTGACCGGCATCGATGA
GGGTCCTCAGCTGGAGGACTACGGTAGCCGATGGCCTACGGTTGTTGCTATGGGACTGGCCGTAGCTACT

CTGGCGGCCGAGCAAACATCTGATCGGCCTGACGGCGCACGGCATGACAAGGTGATAAGCTCGATGGCGAACAAAGCCG
GACCGCCGGCTCGTTTGTAGACCTAGCGTCGGACTGCCGCGTGCTGCAGCTATTCCACTATTCGAGCTACCGCCTTGTTTCGGC

TGGGAGGCGAAGGCCAATGCCTGA
ACCCTCCGCTTCCGGTTACGGACT
```

In a further aspect, the invention relates to a composition for removing nucleic acids from a biological material, which composition comprises a Serratia spp. nuclease. In the present context, the term "biological material" is understood to indicate any material in which at least one component is of biological origin. The term is therefore intended to include a solution of nucleic acids alone (for instance originating from in vitro laboratory work), a fermentation medium containing a cell culture producing a biosynthetic product, a fermentation medium in which a cell culture producing a biosynthetic product has been grown (and which may therefore contain this product as well as nucleic acids originating from spontaneous cell rupture), or a resuspension of a cell culture, which produces a biosynthetic product, after the cells have been harvested from the medium, e.g. by centrifugation, the cell culture comprising either whole or lysed cells.

The term "biosynthetic product" is understood to mean a product which may be a protein, polypeptide, glycolipid carbohydrate or low molecular weight compound. Nucleic acids are particularly important contaminants when the biosynthetic product is not excreted from the cell, necessitating cell lysis in order to harvest the product, in that they impart viscosity to the cell lysate to such an extent that the purification of the product is rendered difficult. To reduce the viscosity of a cell lysate, it is therefore advantageous to provide a composition which contains a nuclease such as a Serratia spp. nuclease of the invention. The nuclease may, for instance, have the amino acid sequence shown above. The nuclease composition of the invention should preferably be substantially free from proteolytic activity as the presence of proteases in a composition of this nature would be a most serious cause of degradation of the proteinaceous products produced by the cell culture. The nuclease prepared by the method of the present invention, the gene coding for which has been obtained from a Serratia spp. organism has in fact been found to be substantially free from proteolytic activity (see Example 2); it should be mentioned that a substantially protease-free composition is particularly important when the composition is to be used to remove residual nucleic acids from an otherwise purified proteinaceous product since, when the nuclease is added to an unpurified cell lysate, the proteolytic activity of the lysate itself will far exceed any proteolytic activity remaining in the nuclease composition. The substantially protease-free nuclease composition is therefore particularly advantageous to use (in substantially pure form, of course) in connection with proteinaceous products which have already undergone several purification steps.

Experiments have shown that even when an excess of nuclease is added to a cell lysate (excessive to a reduction of the viscosity ascribable to the nucleic acid components of the lysate), a minor fraction of nucleic acids may remain to contaminate the proteinaceous product. This is believed to be the result of a "masking" of the nucleic acids, for instance through interactions of nucleic acids with membrane and/or protein components of the lysate. However, complete removal of nucleic acids (defined as the absence of nucleic acids hybridizable by DNA or RNA probes) is often required by the health authorities in several countries (e.g. the FDA) when the biosynthetic products produced by recombinant DNA techniques or from tissue cultures are to be used for medical purposes. When such products are to be used for other purposes where the presence of even minute amounts of nucleic acids might interfere with the desired result, the complete removal of residual nucleic acids is also highly desirable. The present inventors have found that such residual nucleic acids may be completely removed when certain detergents or protein denaturing agents are added together with the nuclease. For applications requiring the complete removal of nucleic acids, it is therefore advantageous that the composition of the invention comprises a nuclease, such as a Serratia spp. nuclease, together with a detergent and/or a chaotropic agent. The detergent may, for instance, be a non-ionic detergent such as a polyoxyethylene alcohol, e.g. Brij® 58 or an octoxynol, e.g. Triton® X-100, or an ionic detergent such as sodium dodecyl sulphate (SDS) or a deoxycholate such as sodium deoxycholate. The chaotropic agent may be selected from urea, thiourea or a salt of thiocyanic acid.

In a still further aspect, the invention relates to a method of removing nucleic acids from a biological material (as defined above), in which a Serratia spp. nuclease is added to the biological material. More particularly, the method of the invention is useful in a variety of situations where contamination with nucleic acids is a problem, such as where the biological material comprises a waste solution or suspension of nucleic acids resulting, for instance, from in vitro experiments with nucleic acids and contaminating laboratory equipment; where the biological material comprises a fermentation medium containing a cell culture producing a biosynthetic product (as defined above), in which case the nuclease may be added before or after cell lysis in a sufficient quantity to secure the removal of the bulk of the nucleic acids in the material; where the biological material comprises a fermentation medium in which a cell culture producing a biosynthetic product has been grown and from which the cells have subsequently been removed, in which case the medium may contain a certain amount of nucleic acids due to spontaneous cell rupture and optionally a biosynthetic product excreted from the cells into the medium; and where the biological material comprises a resuspension of a cell culture producing a biosynthetic product after the removal of the fermentation medium, in which case the nuclease may be added before or after cell lysis. The nuclease may be the one which has the amino acid sequence shown above. The present inventors have found that particularly advantageous results may be obtained when the nuclease of the invention is added to the biological material prior to cell lysis. Experiments have demonstrated that a high degree of reproducibility with respect to the elimination of the viscosity of lysates of, for instance, E. coli (such as freeze-thaw lysates and French Press lysates) is obtained when the nuclease is added to the cell culture (suspended or in medium) prior to cell lysis. Also, a shorter period of time (on the order of minutes rather than hours) and a lower temperature level have unexpectedly been found to be required to attain a certain relative viscosity than when the nuclease is added after cell lysis, which results in a higher yield of the biosynthetic product (for instance, less degradation of a proteinaceous product during removal of nucleic acids).

Many health authorities require that recombinant organisms must be killed prior to being released from the closed fermentation system. In many cases, this is accomplished by adding phenol and toluene during the last phase of the fermentation. It has been found that the nuclease of the present invention retains its activity in the presence of the quantities of phenol and toluene required to kill the cells in the fermentor.

When adding the nuclease to a biological material in accordance with the invention in order to reduce the viscosity of the material, the end product of the nuclease action includes differently sized nucleic acid fragments and oligonucleotides rather than mono- or dinucleotides only. For certain purposes, for instance when it is desired to produce a highly purified end product from which all hybridizable nucleic acids have been removed, it is recommended to add the enzyme to a product which has already been purified, i.e. at least substantially separated from other components of the biological material.

As mentioned above, it has been found that residual nucleic acids, i.e. nucleic acids which remain in a biological material after a limit digest (where nuclease has been added in such excess in order to reduce the viscosity of the material that no further addition of nuclease will reduce the amount of nucleic acids still further), constitute a minute fraction, in fact less than 0.1% of the total amount of nucleic acids in a given biological material and represent nucleic acids which are ordinarily inaccessible to the nuclease due to interactions with membrane components and/or proteins as discussed above. It has been found that if the nuclease treatment is carried out in the presence of a detergent and/or a chaotropic agent, the residual nucleic acids can be digested.

Thus, the invention further relates to a method of removing residual nucleic acids from a biosynthetic product, in which the nuclease is added in the presence of a detergent and/or a chaotropic agent in order to digest the nucleic acids present as oligonucleotides or nucleotides which cannot be detected by hybridization. The detergents and chaotropic agents most likely act by counteracting the hydrophobic and electrostatic forces which are responsible for the formation of a complex structure in which segments of nucleic acids remain inaccessible to the nuclease.

The detergents and chaotropic agents selected should be ones which do not permanently damage the secondary and tertiary protein structure of any desired proteinaceous product present in the biological material, i.e. a substance which may be removed after the nuclease has acted in its presence to remove residual nucleic acids in such a way that the correct structure of the product is obtained. Such detergents and chaotropic agents may, for instance, be the ones mentioned above. When employing a detergent or chaotropic agent, care should also be taken not to incorporate such substances in such amounts that the nuclease activity will be impaired or even eliminated. When the detergent is a non-ionic detergent, it is usually added in an amount of 0.2-1.5%, in particular about 0.4-1.0%, of the biological material. When it is an ionic detergent, it is generally added in an amount of 0.01-1.0% of the biological material. The chaotropic agent is usually added in an amount of 2-8M (about 10-50% w/v of the biological material).

In order to obtain a product which is completely free from nucleic acids, it may be an advantage to first employ the nuclease of the invention at an early stage of the production process in order to reduce the viscosity from a cell lysate and remove the bulk of the nucleic acids present in it. In a subsequent step in the purification procedure, the purified nuclease may be employed in solution or in immobilized form in order to remove any residual nucleic acids from the product.

It is further contemplated that a nuclease-containing composition of the invention may be used to remove the infectious potential of infectious agents either as a means to ensure the elimination of the infectious potential itself or as a means to recover such components of these agents as might be desired to produce vaccines or diagnostic agents. In the present context, the term "infectious agent" is understood to mean a living or non-living agent the infectious potential of which is ascribable to nucleic acid components. These nucleic acid components may encode RNA species and/or proteins essential for the infectious potential (they may, for instance, be needed for propagation), or they may play a purely structural role in the infectious agent. Infectious agents may accordingly include plasmids, viruses, bacteria, prions and parasites.

The infectious potential of these agents may, in some cases, be destroyed by means of chemicals, but it may be an advantage in many cases to use a nuclease for decontamination purposes. Free DNA molecules such as plasmids liberated from cells during growth, may for instance readily be digested by means of the nuclease of the invention, which is also the case with potentially infectious DNA present in waste material from laboratory experiments. As a safety precaution, it may often be desired also to remove nucleic acids from the waste material resulting from the industrial production of biosynthetic products by recombinant DNA techniques. If the nucleic acid component of the infectious agents present in such waste is not freely accessible to the nuclease of the invention, the simultaneous addition of a detergent or chaotropic agent may be recommended as described above in order to remove all nucleic acids present.

A further contemplated use for the nuclease of the invention is in the production of antigens and vaccines. At present, attenuated strains of bacteria and viruses are usually employed to elicit an immunological response to more virulent members of the same species, one important advantage being the preservation of the integrity of complex antigenic structures on the surface of or inside the infectious agent during the limited period of propagation of the agent in vivo. By using the nulease of the invention, it would be possible to preserve the antigenic complexity, permitting the immunological response to be directed against any strong antigenic determinants associated with the infectious agent in question, while avoiding the risk of vaccination sequelae occasionally seen with live vaccines using attenuated organisms. The nuclease of the invention could be used to remove nucleic acid components of such infectious agents, optionally together with a detergent and/or a chaotropic agent to make the nucleic acids available to the nuclease, the detergent or chaotropic agent and the concentration in which they are used being so selected that it does not interfere with the antigenic structure in question.

The Serratia spp. hydrolytic enzymes, produced by the method of the invention, have been found to be expressed at a late stage in the growth cycle of microorganisms producing the enzymes, whether these were Serratia spp. or E. coli. As shown in the Examples, this late expression is a result of the gene expression regulating behaviour of a regulatory region from which expression or the genes in question is initiated. Thus, during most of the exponential growth of the culture, little or no hydrolytic enzyme is synthesized, whereas a high rate of gene expression occurs when the cells enter the late exponential growth phase. In the present context, the term "regulatory region" is understood to mean a molecular sequence involved in the transcriptional control of a gene comprising such sequences as the promoter, any binding sites for regulatory proteins (regulating gene expression), e.g. cyclic AMP binding protein (CAP), and sequences of yet unknown function in transcriptional control, but found, by deletion mapping, to be of importance for transcriptional control.

This regulatory principle may be utilized in accordance with the present invention to provide a plasmid comprising a regulatory region from which expression of a gene located downstream of the regulatory region is initiated or increased at a late stage in the growth cycle of the microorganism harbouring the plasmid. The gene may be one which is not naturally related to the regulatory region.

A regulatory mechanism as described above where gene expression is initiated or increased at a late stage in the growth cycle of the microorganism, is often advantageous and desirable for production cultures. Thus, in a fermentation process, the high cell density occurring late in the fermentation is the potentially most productive period of the culture, and during this period, it may be of great value to have a high rate of gene expression. This is normally not obtained using the known promoters because their activity usually follows the growth rate of the culture, and is therefore minimal at the stage where cell density is highest. The special behaviour of the regulatory regions found in Serratia spp. genes may also be of particular value in cases where the products to be produced by the culture are toxic to the microorganism in question, as the microorganism will only synthesize the toxic product when growth has already or nearly stopped.

Consequently, the present invention further relates to a plasmid which comprises a regulatory region from which expression of a gene located downstream of said regulatory region is initiated or increased at a late stage in the growth cycle of microorganisms harbouring the plasmid. Such a regulatory region is particularly useful for regulating the expression of a gene not naturally related to the regulatory region, such as when the plasmid carrying the regulatory region is to be employed as a cloning or production vector with the object of obtaining, by fermentation of a microorganism harbouring the plasmid, a wide variety of biosynthetic products for technical or medical purposes. Examples of such biosynthetic products are polypeptides and proteins or fragments thereof, enzymes and non-proteinaceous products of reactions of enzymes with a compound in the nutrient medium, low molecular weight products such as hormones, and nucleic acids; products which are contemplated to be of particular interest are products of eucaryotic, especially mammalian genes and, as mentioned above, products which are toxic to the microorganism in which they are produced.

The regulatory region may be one which is found in Serratia spp. genes, although it is contemplated that similar regulatory regions may also be found in other organisms. In particular, the regulatory regions is a nuclease or phospholipase regulatory region from Serratia spp. examples of which are shown in FIG. 7, position 1–385, and FIG. 9, position 201–415, respectively.

A regulatory region as described above may be inserted into any known or new cloning or production vector by means of standard recombinant DNA techniques.

Particularly interesting plasmids useful as cloning or production vectors containing the above-mentioned type of regulatory region are the so-called runaway plasmids, that is, plasmids with a conditionally uncontrolled replication behaviour. Plasmids showing this behaviour are disclosed in, for instance, U.S. Pat. No. 4,495,287 and European Patent Application, Publication No. 0109150.

The strength of the promoter included in the regulatory region of, e.g., the nuclease gene may not always be sufficient for certain production purposes, and therefore the ability of the regulatory region to give rise to growth phase related expression of a gene located downstream from the regulatory region may be further exploited by replacing the present promoter with a stronger constitutive promoter in such a way that the growth phase dependent expression is preserved.

Apart from employing the regulatory region for the expression of a biosynthetic product, a particularly interesting application of the regulatory region is to utilize it to increase transcription of a gene located downstream of the regulatory region, which gene is involved in the control of replication of a bacterial plasmid thereby causing uncontrolled plasmid replication (so-called runaway replication) at a late stage in the growth of cells harbouring the plasmid. Most runaway replication vectors described so far (cf. for instance European Patent Application, Publication No. 0109150) require external manipulation of the growth conditions, e.g., an increase in temperature, to initiate uncontrolled replication. By using the regulatory regions described above to regulate plasmid replication, a novel approach has become possible, namely the initiation of runaway replication as a function of the growth phase of cells harbouring the plasmid. This approach is advantageous from three points of view. Firstly, no external manipulation of the growth conditions is required, secondly, no specific properties of the host cells are required to initiate runaway replication, and thirdly, uncontrolled replication is initiated at a time when the microbial culture enters the late exponential growth phase, that is, when the effect of increasing the copy number of a gene to be expressed is greatest. A preferred regulatory region for initiating runaway replication in the late exponential growth phase is the phospholipase regulatory region due to its dual control systems. One regulatory system ensures that expression of a gene controlled by the phospholipase regulatory region is restricted to the late exponential growth phase; the other regulatory system is able to override the first control system and comprises a glucose repression system.

In the practical exploitation of the regulatory region described above, a DNA fragment carrying both regulatory systems from the phospholipase regulatory region may be inserted into a plasmid upstream of a replication regulatory gene or genes, the plasmid may be transformed to a suitable host microorganism, and transformants may be selected in the presence of glucose. When these transformants are deprived of glucose, they will exhibit the runaway replication phenotype during the late exponential growth phase. A gene expressing a desired biosynthetic product may subsequently be inserted into the plasmids thus produced, the resulting hybrid plasmids may be transformed to a suitable host microorganism, and the host may be grown to a production size culture either in the absence of glucose or in the presence of glucose in such an amount that it is consumed by the cells before they enter the late exponential growth phase; in either case, uncontrolled replication is initiated in the late exponential growth phase due to increased transcription from the regulatory region. The biosynthetic product is harvested from the culture after a suitable period of time to ensure a sufficient production of the product. Apart from the specifics given above, the cultivation is suitably performed using conventional techniques, including conventional nutrient media which are known to be optimal to the microbial species used as the host. Also, the harvesting of the biosynthetic product is performed in accordance with well-known methods adopted to the identity and properties of the particular biosynthetic product, the properties of the host, etc.

The present invention also provides a microorganism harbouring a plasmid which carries a regulatory region as specified above. The microorganism is typically a bacterium such as a gram-negative bacterium, and preferred gram-negative bacteria are ones which are generally employed for the production of biosynthetic products, for instance E. coli.

It is further contemplated that the sequence encoding the N-terminal part of the nuclease, which sequence is indicated to encode a signal peptide essential for transmembrane transport of the nuclease, may be employed to obtain excretion of a gene product. A sequence coding for a desired biosynthetic product may be combined directly with the sequence specifying the C-terminus of the signal peptide of the nuclease thus allowing the desired protein to be excreted, the signal peptide being removed in the process. For practical purposes, the sequence coding for the signal peptide (cf. FIG. 7) may be isolated together with the nuclease regulatory region as a DNA fragment extending from position 1 to 448, with latter position conveniently corresponds to the recognition site for AhaIII and which precisely corresponds to the last codon of the signal peptide (including the signal peptidase recognition site). The DNA fragment may subsequently be inserted into any suitable vector and ligated at the "filled in" (by means of Klenow polymerase) AhaIII site to a sequence coding for a product to be excreted. The optional presence of the nuclease regulatory region further allows the expression to be limited to the late stages of cell growth.

DESCRIPTION OF THE DRAWINGS

The invention is further explained below with reference to the drawings in which

FIG. 7 (comprising 7a and 7b) shows the nucleotide sequence of the 1.3 kB DNA fragment (F2-fragment shown in FIG. 1) carrying the nuclease gene from Serratia W225.

FIG. 9 (comprising 9a–9d) shows the DNA nucleotide sequence of 1.6 Kb of the 3.2 Kb Serratia spp. A1 DNA containing the phospholipase (phl) gene. The positions of a few restriction sites are indicated, CAP with underlined sequences indicates the position of the putative catabolite activator binding site and regulatory region of the phospholipase gene, S.D. indicates the position of a Shine-Dalgarno homology for the ribosomal binding site. The gene starts at position 416 and ends at position 1372.

MATERIALS AND METHODS

Figure 1:
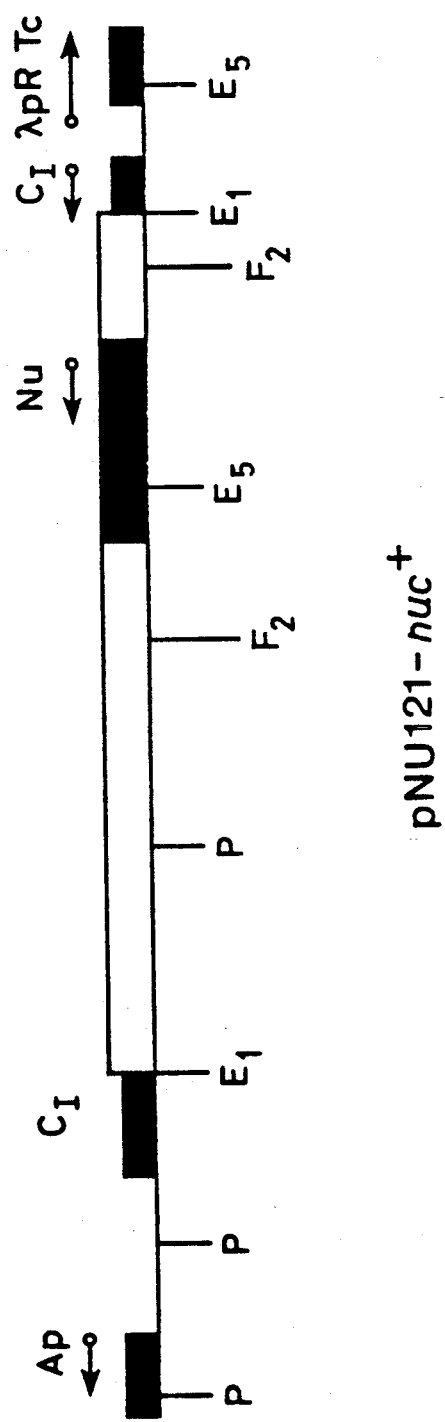
FIG. 1 shows a linear restriction enzyme and genetic map of the hybrid plasmid pNU121-nuc+ carrying the nuclease gene (Nuc) of Serratia marcescens W225. The symbols used are: structural genes ■→=promoters. Ap=ampicillin resistance; Tc=tetracycline resistance; C$_l$=lambda repressor gene, λpR=lambda promoter. P=PstI; E1=EcoRI; E5=EcoRV; F2=FnuDII.

The strains of Escherichia coli K-12 and Serratia marcescens W225 are listed in Table 1. Plasmids and bacteriophages used are listed in Table 2.

TABLE 1

| | Bacterial Strains Used | |
|---|---|---|
| Bacterial Strains | Genotype | Reference/Source |
| E. coli K-12 MT102 | thi, ara-levΔ7679, ara D139, lacΔ × 74, galU, galK, rpsL, hsdR. | |
| E. coli K-12 CSH50 | Δpro-lac, rpsL | J. Miller: Experiments in Molecular genetics, CSH Lab., Cold Spring Harbor, 1972. |
| E. coli K-12 W3110 | tna trp | S. G. Shogman & J. E. Sjöström, J. Gen. Microbiol. 130, 1984, p. 3091. |
| E. coli K-12 JM103 | Δlac pro, thi, strA supE, endA, sbcB15, hsdR4, F'tra D36, proAB, lacI$^q$ zΔM15 | J. Messing, Nucl. Acids Res. 9, 1981, pp. 309–321 |
| E. coli K-12 S17 | thi, pro, hsdR, hsdM+, recA | R. Simon, Bio/Technology, November 1983 |
| Serratia marcescens W255 | Tc$^R$ | U. Winkler, Molec. gen. Genet. 124, 1973, |

TABLE 1-continued
Bacterial Strains Used

| Bacterial Strains | Genotype | Reference/Source |
|---|---|---|
| | | pp. 197-206. |

TABLE 2
Plasmids and Bacteriophages Used

| Name | Relevant Phenotype | Reference/Source |
|---|---|---|
| pNU121 | $Ap^R$, pBR322 derivative | B. Nielsson: Nucl. Acids Res. II, 1983, pp. 8019-8030 |
| pOU57 | R1 "runaway replication" derivative, $Ap^R$ | J. E. L. Larsen, Gene 28, 1984, pp. 45-54 |
| pGV403 | $Cm^R$, pBR322 derivative | Amersham Ltd. |
| pACYC177/ cI857 | $Kan^R$, derivative of pACYC177 carrying λcI857 | Chang & Cohen, J. Bacteriol. 134, 1978, pp. 1141-1156 |
| pLc28 | $Ap^R$, pBR322 derivative | E. Remaut et al., Gene 15, 1981, p. 81 |
| M13 mp8 and mp9 | Phage M13 derivatives for DNA nucleotide sequencing | Amersham and J. Messing. Nucl. Acids Res. 9, 1981, pp. 309-321 |

All experimental techniques used were standard techniques as described in T. Maniatis: *Molecular Cloning*, Cold Spring Harbor Laboratory, 1982, and J. Miller: *Experiments in Molecular Genetics*, Cold Spring Harbor, 1972.

All cells were grown in LB medium (Bertani, *J. Bact.* 62, 1951, p. 293) or in A+B minimal medium (Clark and Maaløe, *J. Mol. Biol.* 23, 1967, p. 99), with addition of vitamins and amino acids. Plates for bacterial growth contained LB medium and 1.5% agar with or without antibiotics: Tetracyclin 8 μg/ml, ampicillin 50 μg/ml, chloramphenicol 20 μg/ml. Plates for screening for nuclease activity contained DNase test agar (Difco) for DNase activity.

EXAMPLE 1

Preparation of chromosomal DNA from *Serratia marcescens* W225

A culture of *Serratia marcescens* W225 was deposited in the DSM (Deutsche Sammlung von Mikroorganismen, Grisebachstrasse 8, D-3400 Göttingen, West Germany) on May 8, 1985 under the Accession No. 3308). The culture was grown overnight in LB medium and harvested by centrifugation (8,000 r.p.m. for 5 minutes). The cells were washed twice in TEN-buffer (10 mM Tris, HCl, pH 8, 1 mM EDTA, 100 mM NaCl) and resuspended in 20 ml TEN-buffer containing 1 mg/ml lysozyme and 0.1 mg/ml RNase. The cells were incubated at 37° C. for a period of 30 minutes and 20% SDS was added to a final concentration of 1%. After 60 minutes at a temperature of 37° C. (for total lysis), the lysate was incubated at a temperature of 4° C. overnight. Next day the cell debris was removed by centrifugation (18,000 r.p.m. for a period of 25 minutes). The supernatant was transferred to a new tube containing 2 ml 3M sodium acetate and 2 volumes of isopropanol. Upon gentle mixing, the DNA precipitated in threads which were picked up by means of a curved glass needle. The precipitated DNA was washed twice in 80% ethanol and resuspended in TEN-buffer. The DNA was further purified by buoyant density gradient centrifugation, and after appropiate dilution it was extracted with phenol and dialysed against TE-buffer (10 mM Tris-HCl, pH 8, 1 mM EDTA). Finally, the DNA was tested for absence of nuclease by incubation at 37° C. with restriction enzyme buffer.

Construction of a gene bank from *Serratia marcescens* W225.

The cloning vector plasmid, pNU121, was used in connection with the construction of a gene bank from *Serratia marcescens* W225. The plasmid is a pBR322 derivative coding for both ampicillin resistance and tetracyclin resistance, but the promoter of the tetracyclin resistance gene is replaced by the phage λ promoter, λpR, and since the λ repressor gene, $C_I$, is also present on pNU121, tetracyclin resistance is normally not expressed. Resistance is, however, expressed if the $C_I$ gene is destroyed by insertion of DNA into the $C_I$ gene.

Therefore, pNU121 DNA having a unique EcoRI site in the $C_I$ gene was digested with the restriction enzyme EcoRI and mixed with *Serratia marcescens* DNA partially digested with EcoRI. The DNA was ligated at 15° C. overnight with T4 ligase and transformed to *E. coli* strain MT102. Selection was made at 37° C. on LB plates containing 8 μg/ml tetracyclin, so only cells harbouring pNU121 with inserted DNA will give rise to colonies. Approximately 2,500 colonies representing a gene bank of *Serratia marcescens* W225 were isolated by this procedure.

Isolation of a nuclease gene from *Serratia marcescens* W225

The gene bank from *Serratia marcescens* W225 was replica plated onto DNase indicator plates (see Materials and Methods) and after growth at 37° C. for two days, the plates were developed with 0.1N HCl. DNase positive colonies were surrounded by a clearing zone. One positive clone, pNU121-nuc+, was re-isolated from the master plate and tested for the presence of other genes coding for extracellular enzymes. (*Escherichia coli* MT102/pNU121-nuc+ was deposited in the DSM on May 8, 1985 under the Accession No. 3309.) The clone was found to express RNase too, but no other extracellular enzymes were expressed from the clone. The EcoRI fragment carrying the nuclease gene was also inserted into the runaway cloning vector pBEU50 resulting in the plasmid pBEU50-nuc+. (*Escherichia coli* C600/pBEU50-nuc+ was deposited in the DSM on May 8, 1985 under the Accession No. 3310.)

Restriction enzyme mapping of the nuclease gene

Plasmid DNA from *E. coli* strain MT102 harbouring the nuclease gene was prepared and digested with the restriction enzymes EcoRI, PstI and EcoRV, respectively. The digested fragments were analyzed by agarose gel electrophoresis resulting in the map shown in FIG. 1. The DNA digested with PstI was religated with T4 DNA ligase and transformed to strain MT102. Selection was made on DNase indicator plates containing 8 μg/ml tetracyclin. After incubation, the plates were developed and all colonies showed a nuclease positive phenotype. When the DNA digested with EcoRV was religated and transformed to MT102, selecting for ampicillin resistance, all transformants were nuclease negative. Therefore, the nuclease gene is carried on a 2 Kb PstI-EcoRI fragment as shown in FIG. 1.

For further subcloning, the plasmid DNA was digested with both PstI and EcoRI, and after electrophoresis the PstI-EcoRI fragment carrying the nuclease gene was purified from the gel. The DNA was partially digested with the restriction enzyme FnuDII (a 4-base blunt end restriction enzyme with several cleavage sites in the nuclease gene) and mixed with DNA from plasmid pGV403, which had been digested with the restriction enzyme SmaI. The mixed DNA was ligated with T4 ligase and transformed to MT102. Selection was made on LA plates containing 20 µg/ml chloramphenicol (resistance of pGV403), and the transformants were replica plated onto DNase indicator plates. Twenty nuclease positive colonies were isolated and plasmid DNA prepared. The smallest plasmid had a 1.3 Kb DNA insertion, and the insert was mapped with respect to the EcoRV site as shown in FIG. 1. This plasmid was denoted pGV403-SD2/10. A plasmid carrying the same insert but in the opposite orientation with respect to the unique EcoRI and HindIII recognition sites of pGV403 was denoted pGV403-SD2/14.

Nucleotide sequence of the nuclease gene

The method of Maxam and Gilbert was used (Proc. Natl. Acad. Sci USA 74, 1977, pp. 560–64), using the sequencing vector plasmid pGV403 (Amersham). The DNA to be sequenced is inserted into the SmaI site of the vector. The SmaI is flanked by two restriction sites for restriction enzyme Tth111I, which gives different 5-prime overhanging ends, and since the enzyme cleaves assymmetrically, the DNA can be sequenced directly after labelling with $^{32}$P.

Therefore, the 1.3 Kb nuclease fragment originally cloned into the SmaI site of pGV403 was isolated from an agarose gel after digestion of the hybrid plasmid with Tth111I. The DNA fragment was digested with one of the restriction enzymes FnuDII or HaeIII and ligated to pGV403 DNA cleaved with SmaI and dephosphorylated. The DNA was then transformed to MT102, and selection was made on LA plates containing 20 µg/ml chloramphenicol. Plasmid DNA from the transformants was prepared and analysed. In this way, a series of pGV403 hybrid plasmids was constructed with insertion of DNA from 200–400 bp covering the whole 1.3 Kb fragment, and sequencing of these plasmids in both strands gave the nucleotide sequence shown above.

Analysis of the nucleotide sequence shown in FIG. 7 indicates that the nuclease is coded from position 386 to 1165. Firstly, an open reading frame extends throughout this region which would encode a protein of 30,000 daltons. Secondly, a perfect ribosome binding site is present at position 374–78, i.e. just upstream of the initiation codon. Thirdly, sequences which may constitute a regulatory region are present at position 330 to 336 ("−10 sequence") and position 306 to 313 ("−35 sequence").

To confirm that the nuclease is in fact encoded by the indicated sequence rather than from a long open reading frame present on the complementary strand, the inserts in pGV403-SD2/10 and pGV403-SD2/14 were excised by double digestion with EcoRI and HindIII. It should be noted that the orientations of the inserts are opposite relative to the two restriction sites of the pGV403 vector. The excised fragments were ligated to pPL195 which had been double digested with EcoRI and HindIII. The vector pPL195 is derived from pLc28 by inserting a polylinker containing EcoRI and HindIII recognition sites downstream from the λpL promoter. Following transformation into E. coli NF1 and selection at 30° C. for Ap$^R$, two plasmids were isolated, pPL195-SD2/10 and pPL195-SD2/14. In the former, the λpL promoter is located upstream of the putative nuclease coding region depicted above, while in the latter plasmid the λpL promoter is located in such a way that the complementary strand will be transcribed. E. coli NF1 is lysogenic for a defective λ coding for the temperature-sensitive λ repressor encoded by the cI857 gene. At 30° C. the cI repressor is active, and promoters regulated by the repressor such as λpL present on pPL195 are thus repressed. At temperatures above 37° C., the repressor is inactive and transcription from λpL in pPL195 will occur. When comparing the nuclease activity at 30° C. and 42° C., pPL195-SD2/10 but not pPL195-SD2/14 gave rise to temperature inducible nuclease synthesis indicating that the orientation of the nuclease-coding region relative to the λ promoter is correct in pPL195-SD2/10.

Furthermore, high levels of (temperature inducible) nuclease synthesis were obtained when the predicted nuclease coding region was joined directly to the λ promoter. An RsaI-HindIII fragment from pGV403-SD2/10 spanning the region from position 357 to 1295 (FIG. 7) was ligated to pPL 195 digested with SmaI and HindIII whereby the coding region is positioned as in pPL195-SD2/10 relative to the λ promoter. This plasmid was denoted pPL195-SD2/RI.

The nucleotide sequence corresponding to the amino terminus of the nuclease has been confirmed by amino acid sequence analysis of the partially purified protein. The nucleotide sequence corresponding to the carboxy terminus of the nuclease has been verified by nucleotide sequencing of the region using an alternative sequencing method, the dideoxy nucleotide sequencing of Sanger et al., Proc. Nat. Acad. Sci. USA 74, pp. 5463–5467.

The predicted amino terminal sequence of the nuclease indicates the presence of a signal peptide of 20 amino acids which is terminated by a recognition sequence for a signal peptidase at position 448.

Enzyme activities of nuclease

Cultures of Serratia marcescens strain W225 and E. coli C600 harbouring the plasmid pBEU50-nuc$^+$ were grown exponentially in LB medium at 30° C. At various times one ml samples were taken for determination of $OD_{450}$ and nuclease activity. Nuclease activity was determined by adding 100 µl chloroform to release enzymes from the periplasm. After centrifugation at 10,000 r.p.m. for 15 min., 25 µl of the supernatant was taken for determination of nuclease activity. The sample containing nuclease was added to 0.5 ml of salmon sperm DNA (1 mg/ml) dissolved in 0.05M Tris (pH 8.0) +0.01M $MgCl_2$, and the mixture was incubated at 37° C. for one hour. Then 0.5 ml 4% PCA (perchloric acid) was added and left on ice for 30 min. The precipitate of undigested DNA was removed by centrifugation, and $OD_{260}$ (absorption of UV light at wave-length 260 nm) was measured on a spectrophotometer in a quartz cuvette. The activities presented in Table 3 are $OD_{260}$ values measured in this way from samples of the cultures growing into the stationary phase. It appears that in both cultures, the enzyme is preferentially synthesized in the late phase of the growth cycle.

TABLE 3

| Strain | Nuclease activity | |
|---|---|---|
| | Cell Density (OD$_{450}$) | Extracellular Nuclease Activity |
| C600/(pBEU50-nuc$^+$) | 0.265 | 0 |
| | 0.448 | 0.005 |
| | 0.628 | 0.075 |
| | 0.800 | 0.135 |
| | 0.940 | 0.222 |
| | 1.28 | 0.447 |
| | 1.63 | 1.04 |
| | 2.50 | 1.78 |
| | 3.15 | 2.87 |
| | 4.20 | 3.90 |
| | 4.80 | 5.90 |
| | 5.10 | 7.70 |
| | 5.95 | 12.1 |
| | 6.80 | 14.2 |
| | 7.45 | 15.9 |
| | 8.08 | 35.2 |
| W225 | 0.240 | 0 |
| | 0.386 | 0 |
| | 0.608 | 0 |
| | 0.865 | 0 |
| | 1.01 | 0 |
| | 1.48 | 0 |
| | 2.03 | 0 |
| | 2.56 | 0 |
| | 3.51 | 0.047 |
| | 4.30 | 0.555 |
| | 7.10 | 2.1 |
| | 9.50 | 4.6 |
| | 10.60 | 5.0 |
| | 11.4 | 6.7 |
| | 14.0 | 7.0 |
| | 14.7 | 7.1 |

In a parallel experiment, the distribution of nuclease between periplasm and growth medium was measured by dividing culture samples into two parts: One containing only cell-free growth medium, and the other containing material from both periplasm and growth medium (chlorophorm treatment as described above). The results are shown in Table 4.

TABLE 4

| Strain | Nuclease Activity | |
|---|---|---|
| | Periplasm | Growth Medium |
| Serratia marcescens W225 | 1.0 | 45.8 |
| C600/pBEU50-nuc$^+$ | 1.5 | 1.23 |

As shown above, in *Serratia marcescens* W225 essentially all nuclease is totally excreted whereas only approx. 50% is excreted from *E. coli*.

EXAMPLE 2

Purification of nuclease

After 16–20 hours in the stationary growth phase, the fermentation medium from 25 liter cultures of *E. coli* MT102 containing plasmid pGV403-SD2 (described in Example 1) was harvested by ultrafiltration across a 0.45 μm membrane followed by concentration by ultrafiltration across a filter with a cut-off at 10,000 daltons. After dialysis against 10 mM Tris-HCl (pH 7.5), 1 mM EDTA, the preparation was filtered through a glass filter, and a 0.45 and 0.22 μm filter.

The enzyme preparation was tested for various parameters in a standard assay which is summarized as follows:

400 μl buffer comprising 50 mM Tris (pH 8.2), 1 mM MgCl$_2$, 50 μg/ml BSA, 100 ml DNA solution (5 mg/ml salmon sperm DNA in water) and 25 μl diluted enzyme preparation in the above buffer (without DNA) were incubated for 60 minutes at 37° C. To the reaction mixture were added 400 μl 4% cold perchloric acid. The reaction mixture was left standing on ice for 30 minutes and then centrifuged at 15,000×g for 5 minutes. The absorption was measured at 250 nm. 1 unit is defined as the activity which in the standard assay releases 1 OD$_{260}$ of soluble material per ml of DNA in 1 hour.

To determine the pH-optimum, the pH of the standard assay buffer was varied and measured after the addition of DNA. The optimum range for nuclease activity is 7.5–9.6 with a maximum at pH 8.5–9.2. The Mg$^{2+}$ optimum was determined by varying the concentration of MgCl$_2$ in the standard assay from 0 to 100 mM. There is a relatively clearly defined optimum in the range of 0.1–1 mM MgCl$_2$. However, the enzyme retained about 40% of its activity without addition of MgCl$_2$. The optimum concentration of monovalent cations was determined by varying the concentration of NaCl and KCl in the standard assay. The activity decreased rapidly at increasing Na$^+$ concentrations. The enzyme was shown to be active at 0–50 mM of KCl (there was no decrease in activity), which is important as cell lysis, especially of *E. coli*, yields a rather high quantity of K$^+$ as the intracellular concentration is 100–150 mM K$^+$. Short-term enzyme stability was determined by pre-incubating the enzyme in the standard assay buffer without any DNA at 4, 23 and 37° C. for 1, 4 and 18 hours, respectively. On addition of DNA, the enzyme activity was determined in the standard assay. Table 5 below shows the observed value for absorption at 250 nm in the standard assay. A stable enzyme will show the same values in each column.

TABLE 5

| Preincubation | 4° C. | 23° C. | 37° C. |
|---|---|---|---|
| 1 hour | 0.389 | 0.445 | 0.442 |
| 4 hours | 0.415 | 0.485 | 0.403 |
| 18 hours | 0.455 | 0.505 | 0.298 |

It appears from Table 5 that at 4° and 23° C., the enzyme is stable for 18 hours in the buffer. At 37° C. there is a decrease in activity on incubation for a longer period of time.

The effect of denaturing agents was determined by testing the activity of the enzyme in the presence of urea, non-ionic detergents (Brij ® 58, Triton ® X-100) and ionic detergents (SDS and sodium deoxy cholate). These substances were added to the preparation in the standard assay at different concentrations. The enzyme was found to be active in 1–8M urea, the enzyme actually showing an increased activity at 4–8M with a maximum at 4M urea. The enzyme was also fully active in the presence of non-ionic detergents such as Brij ® 58 (1%) and Triton ® X-100 (0.4%). With respect to ionic detergents, an SDS concentration of more than 0.01% leads to a complete inhibition of enzyme activity, while about 40% activity was retained in the presence of 1% sodium deoxy cholate.

The purity of the enzyme was analyzed by means of a standard denaturing SDS-PAGE. The enzyme preparation contained a number of protein bands. In the area corresponding to the apparent molecular weight of the nuclease (30,000), there was a distinct band estimated to represent 5–10% of the entire preparation.

Protease activity in the nuclease preparation was estimated by different assays. Firstly, 50 μl nuclease samples were spotted in water on protein (skim milk)

agar plates (20% milk in buffer). No formation of a clearing zone (degradation of the milk proteins on the plate) was observed after 24 hours at 37° C. and 48 hours at 23° C.

Secondly, no measurable degradation of azo-casein was observed on incubating 20 μl of the enzyme with 1 mg of azo-casein (buffer: 50 mM Tris (pH 8.0), 10 mM $MgCl_2$)) at 0, 16 and 30° C. for 12 hours, followed by measuring acid soluble azo dye at $A_{370}$. Thirdly, nuclease incubated at 37° C. in the presence of 5 mM $MgCl_2$ was analyzed by SDS-PAGE. No change in the pattern of the approximately 20 proteins present in the nuclease preparation, i.e. no autoproteolysis, was observed, indicating the absence of proteases. This means that in the practical application of the nuclease, a possible low content of proteolytic activity in the enzyme preparation will be minimal compared to the total content of protease in the cell lysate to be treated.

The ability of the nuclease to degrade DNA and RNA in the presence of organic solvents was determined. To aliquots of an FTL-lysate of E. coli MT 102 (1 part by volume of cells to 1 part by volume of Tris-EDTA buffer to which had been added 12,000 units of nuclease per ml prior to cell lysis, cf. Example 3 below) were further added phenol (1%), toluene (1%), chloroform (1%), ethanol (5%), or EDTA (0.25M). After incubation at 20° C. for 4.5 hours, the samples were analyzed by agarose gel electrophoresis. The sample to which EDTA had been added served as a control since the nuclease is virtually inactive at this concentration of EDTA. The addition of the various organic solvents did not affect the activity of the nuclease when compared to a sample to which no organic solvents had been added, and 95% of the DNA was degraded to fragments of 200 bp or less.

EXAMPLE 3

Reduction of viscosity in a cell lysate

The enzyme produced in Example 2 was added to a highly viscous FTL (lysozyme-freeze-thaw) lysate of 0.27 g E. coli at a total volume of 500 μl at about $2.6 \times 10^2$ and $2.6 \times 10^3$ units, respectively. To a series of samples, no $Mg^{2+}$ had been added, while 10 mM $Mg^{2+}$ had been added to another series of samples. The samples were incubated at 0° or 24° C.

Table 6 below shows the time at which the cell lysate was "aqueous", i.e. apparently having a viscosity approaching that of water (determined by aspirating a sample of the lysate into a pipette and observing whether the lysate runs out of the pipette as separate non-viscous drops).

TABLE 6

| Temperature | $Mg^{2+}$ | Time after addition of enzyme (minutes) | |
|---|---|---|---|
| | | $2.6 \times 10^2$ units | $2.6 \times 10^3$ units |
| 0° C. | — | 72 | 12 |
| | +10 mM | 55 | 8 |
| 24° C. | — | 55 | 5 |
| | +10 mM | 40 | 3 |

It should be noted, however, that considerable variations were observed in experiments involving different lysates. For instance, when FP (French Press) lysates were used, a certain degree of shearing of the nucleic acids was obtained. This type of lysate was found to provide a better substrate for the enzyme which is probably due to the less tightly packed gel structure of the FP lysate. The viscosity of an FP lysate (15 ml) obtained from 7.5 g of E. coli W3110 (wet weight) was reduced to "aqueous" on incubation of the lysate at 0° C. with 24 enzyme units/ml for 40 minutes.

Addition of nuclease prior to cell lysis

A. To 0.25 g of E. coli MC 1000 (wet weight) resuspended in 0.25 ml of TE (TE=10 mM Tris (pH 8.0), 1 mM EDTA) were added 12 units of the nuclease produced in Example 2. The suspension was subjected to FTL lysis according to standard procedures (3 cycles of freeze-thawing). The viscosity was monitored visually, the appearance of "aqueous" drops by pipetting being taken as an indication of a reduction of the viscosity of the lysate. After the last FTL cycle, the lysate was incubated at 0° C. After 5 minutes at 0° C., the lysate had become "aqueous".

This experiment unexpectedly showed the beneficial effect of adding the enzyme prior to cell rupture as only 24 enzyme units per ml are required to reduce the viscosity in 5 minutes if the nuclease is added before lysis compared to a requirement of 5200 units per ml of lysate in 12 minutes if the nuclease is added after lysis.

B. To obtain a better quantitation of the reduction of viscosity, this procedure was tested on E. coli lysates made by X-PRESS (Biotec) which combines freeze-thaw effects and high pressure lysis.

7.5 g of E. coli MC 1000 (wet weight) were resuspended in 7.5 ml of TE. $MgCl_2$ was added to 2 mM and nuclease to 25 units/ml. The suspension was frozen in the X-PRESS and subjected to five pressure cycles at −20° C. The homogenate was thawed at 0° C. over a period of 2 hours. Visually, the viscosity had been reduced at the time of thawing (i.e. "aqueous" drops by pipetting), but the extended period of thawing makes it difficult to establish a time zero prior to which the nuclease is not active. 24 units per ml of lysate are therefore useful to reduce the viscosity of X-PRESS lysates if the nuclease is added before lysis.

Figure 2:
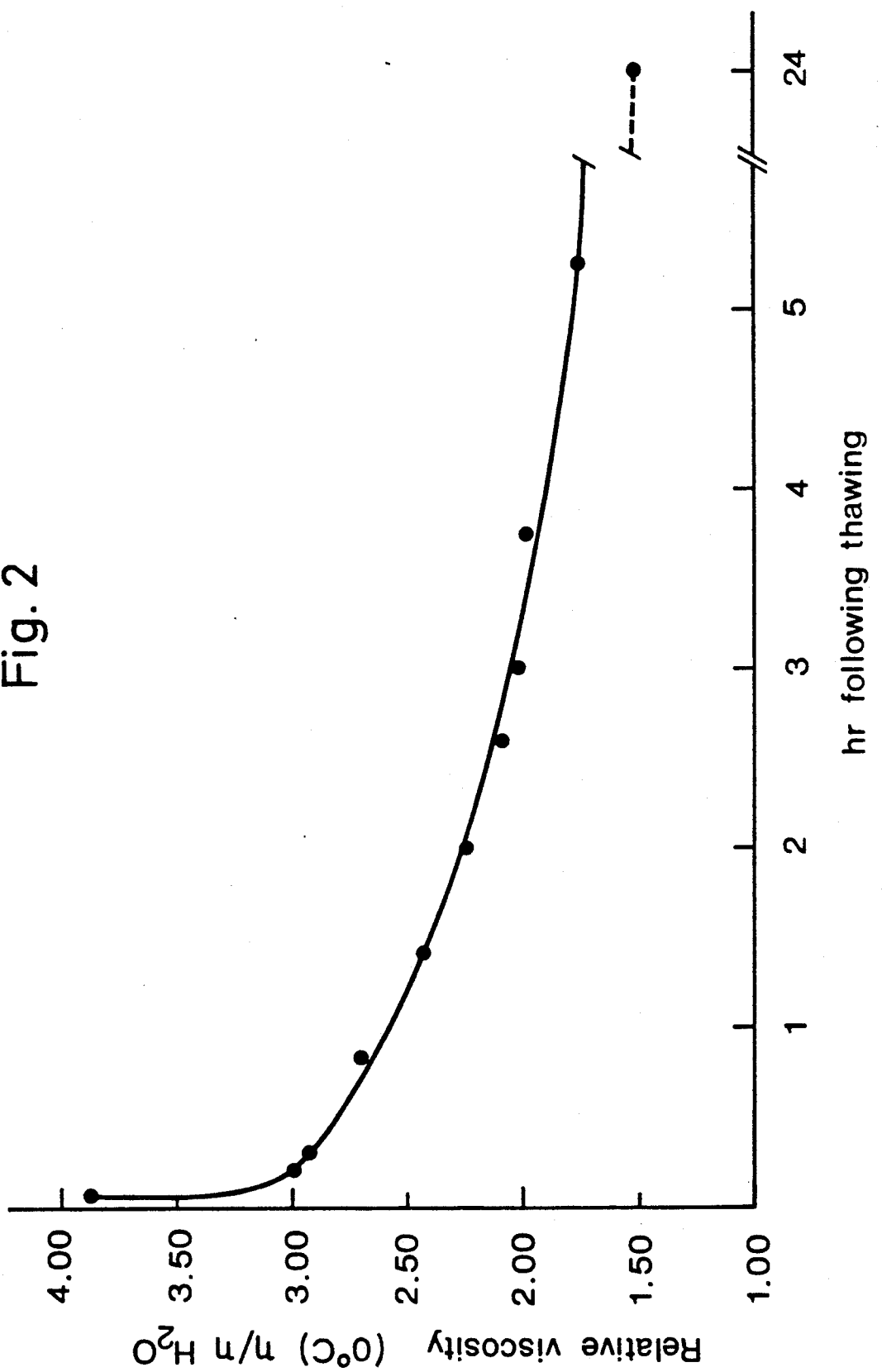
FIG. 2 shows the time course of nuclease treatment of X-PRESS lysate of E. coli. Ordinate: relative viscosity (H$_2$O at 0° C. as reference). Abscissa: hours of incubation at 0° C. following X-PRESS lysis.

The homogenate was diluted to 37.5 ml with TE (0° C.), and the viscosity was monitored (Ostwald viscosimeter) for the next 24 hours. The nuclease digestion was continued in the viscosimeter which was incubated at 0° C. At the time indicated in FIG. 2 (abscissa), the viscosity was determined. The ordinate in FIG. 2 shows the observed viscosity relative to the viscosity of $H_2O$ at 0° C. The reaction conditions were 9.6 units of nuclease per ml of lysate. The relative viscosity decreases rapidly during the first 10 minutes followed by a steady decrease during the subsequent hours of incubation at 0° C. At 24 hours the relative viscosity was 1.5.

C. 7.5 g of E. coli MC 1000 (wet weight) were resuspended in 7.5 ml of TE. $MgCl_2$ was added to 6 mM and nuclease to 24 units/ml. Bacteria plus enzyme was passed through a French Pressure Cell at 10,000 psi. The lysate was immediately incubated at 0° C. Time zero was taken as time of release from press. Upon release the lysate yielded "viscous" drops by pipetting which, however, changed to "aqueous" drops within 5 minutes of incubation at 0° C.

24 units of lysate are therefore also useful to reduce the viscosity of FP lysates.

Figure 3:
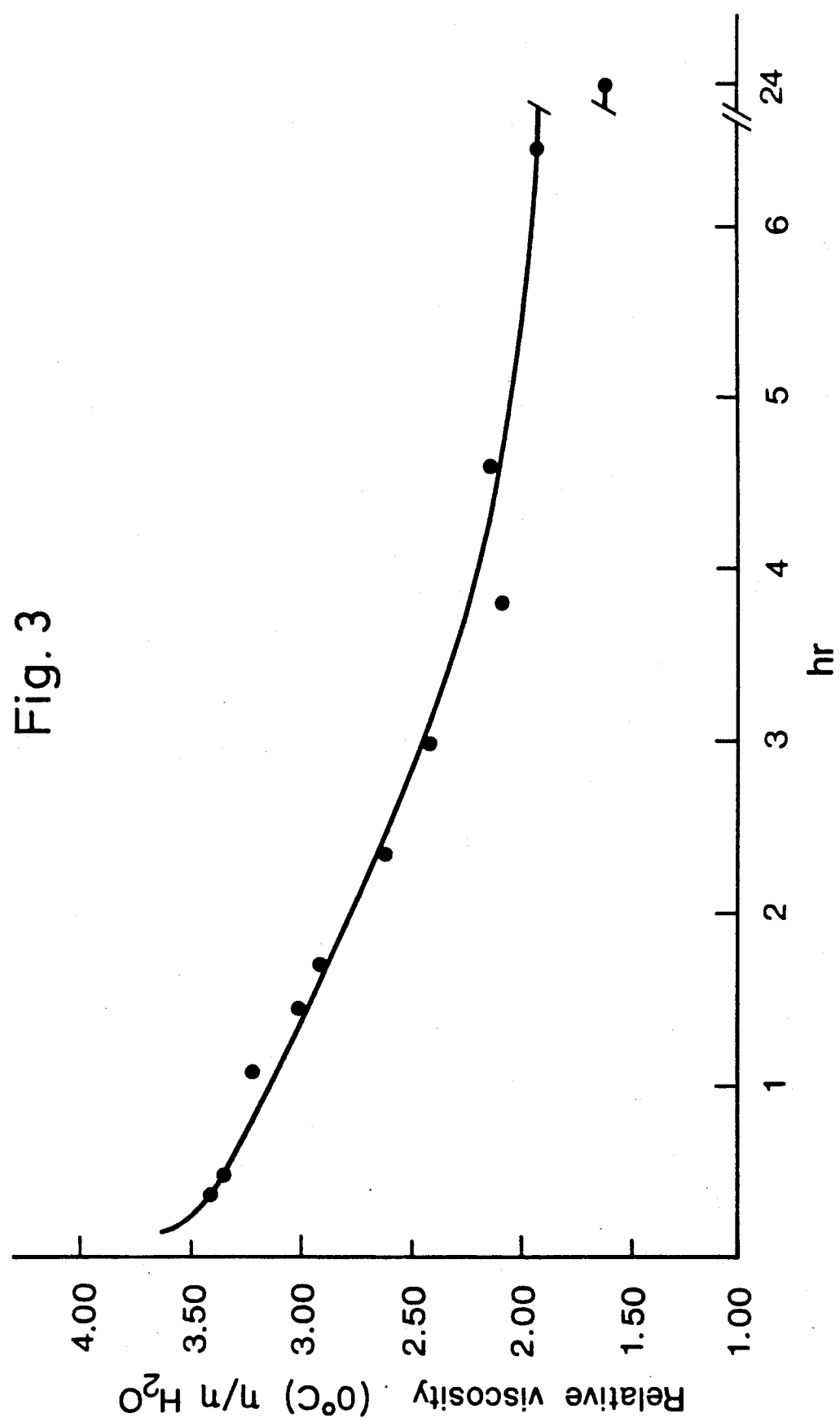
FIG. 3 shows the time course of nuclease treatment of French Press lysate of E. coli. Ordinate: relative viscosity (H$_2$O at 0° C. as reference). Abscissa: hours of incubation at 0° C. following French Press lysis.

At 5 minutes the lysate was diluted to 30 ml with TE (0° C.), and the viscosity was determined in the Ostwald viscosimeter at different times (FIG. 3, abscissa). The result is given as the relative viscosity (ordinate) using the viscosity of $H_2O$ at 0° C. as reference. The reaction conditions in the viscosimeter were: 12 units of nuclease per ml of lysate from 0.25 g of *E. coli* MC 1000 per ml, temperature=0° C.

Figure 4:
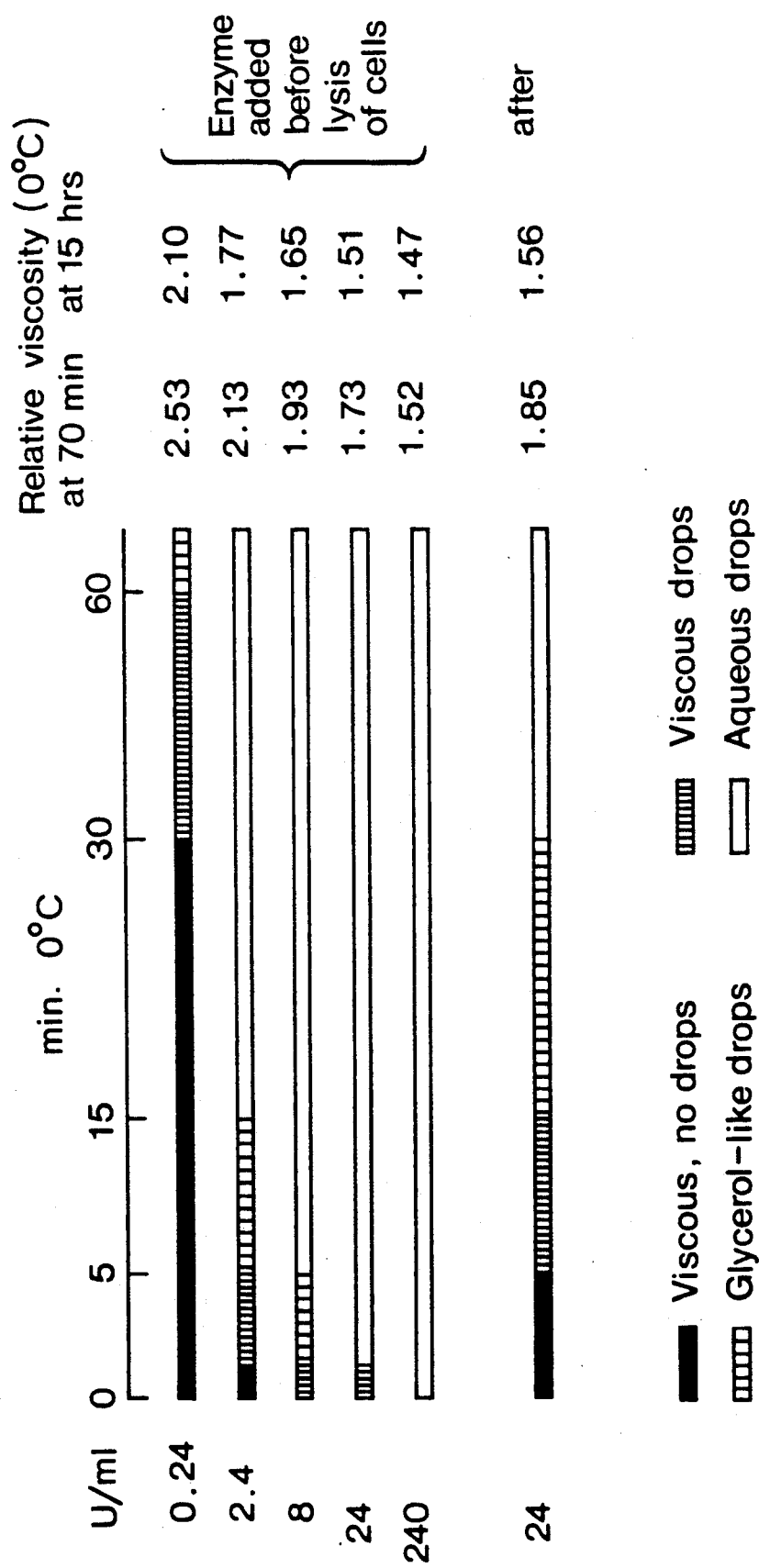
FIG. 4 shows the time course of nuclease treatment of French Press lysate of E. coli. Left column indicates the concentration of nuclease (U/ml) added before or after cell lysis. Six samples were followed individually in time course experiments (minutes of incubation at 0° C.); zero time corresponds to release from French Press. Visual estimation of viscosity was carried out from 0–70 minutes as indicated in each line, cfr. symbols given below lines. The relative viscosity (H$_2$O at 0° C. as reference) was measured at 70 minutes and 15 hours of incubation at 0° C.

To illustrate the advantageous effects of adding the nuclease prior to lysis, the following experiment was carried out. Lysates were prepared as described above. To 15 ml samples of a suspension of *E. coli* W 3110 (7.5 g of cells) were added varying amounts of nuclease to final concentrations of 0.24 to 240 units per ml (lines 1 to 5 in FIG. 4). Following lysis by French Press, the lysates were incubated at 0° C., and the viscosity was followed visually, i.e. by pipetting. The classification is depicted in FIG. 4.

At 240 units of nuclease per ml (line 5), the lysate was "aqueous" upon release from the press while the presence of nuclease at a concentration of 2.4 units per ml (line 2) yielded "aqueous" drops after approximately 20 minutes at 0° C. At 0.24 units per ml (line 1), the result at 70 minutes was "glycerol-like" drops which changed to "aqueous" drops during the subsequent 15 hours of incubation at 0° C.

The relative viscosity of 2.5 fold dilutions of the above samples was determined after 70 minutes and 15 hours of incubation at 0° C. Lines 2–5 show that in this experiment the visual impression "aqueous" drops spans a range of 1.5 to 2.1 in relative viscosity. With an excess of enzyme (line 5), the minimum value obtainable is 1.5. This minimum is presumably reached at 70 minutes, indicating that the component of the viscosity ascribable to nucleic acids has been removed.

Figure 5:
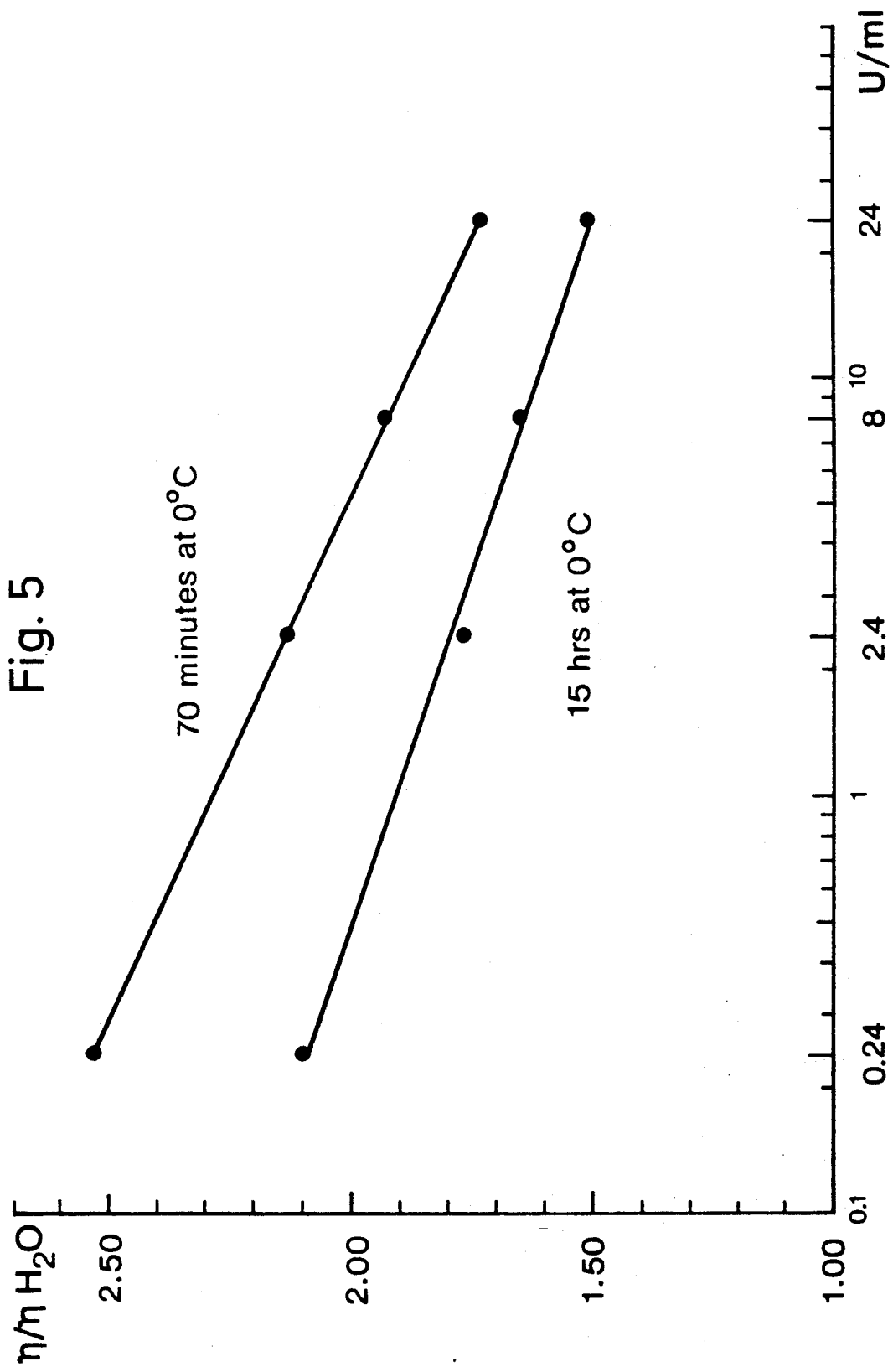
FIG. 5 shows the relationship between relative viscosity (H$_2$O at 0° C. as reference) (ordinate), concentration of nuclease (abscissa), and duration of incubation at 0° C. The figures is a representation of the data given in FIG. 5. Note that the abscissa is log-scale.

To provide information on the amount of nuclease needed in specific applications, the relationship between the amount of enzyme added and the viscosity at 70 minutes and at 15 hours was plotted (FIG. 5). Addition of 3,600 units of nuclease yielded approximately the same value at 70 minutes and 15 hours of incubation at 0° C., namely 1.52 and 1.47, respectively. The value 1.50 may therefore be taken as the minimum value for the relative viscosity of the lysate in question.

After incubation for 70 minutes at 0° C., the relative viscosity is proportional to log(enzyme added) or log-(enzyme concentration). By extrapolation, the additon of 1,500 units (100 units per ml) would completely eliminate the viscosity component of the lysate that can be ascribed to the presence of nucleic acids, i.e. addition of enzyme in excess of 1,500 units or extension of the incubation period would yield no further reduction in the relative viscosity, the minimum value of which is 1.5.

It appears from the figure that a 10 fold reduction in the amount of enzyme added requires a 10 fold prolongation of incubation at 0° C. in order to achieve the same viscosity (e.g. 36 units/70 minutes vs 3.6 units/15 hours, 360 units/70 minutes vs. 36 units/15 hours.

To compare the new strategy of adding nuclease prior to cell rupture with the traditional method of adding nuclease after lysis of the cells, a 15 ml lysate was prepared as above but no nuclease was added prior to cell rupture. After French Press lysis, 360 units of nuclease were added to a final concentration of 24 units per ml, and the lysate was incubated at 0° C. Line 6 in FIG. 4 shows the stepwise elimination of visocity with the appearance of "aqueous" drops at 40 minutes. The relative viscosity at 70 minutes was comparable to that of the sample shown in line 3 (8 units per ml added before lysis), although the initial rate of reduction of viscosity is clearly different. It is estimated that the addition of approximately 1.5 units of nuclease per ml before cell lysis would yield a time pattern identical to that of line 6 but the resulting relative viscosity would clearly be higher, in the range of 2.13–2.53. The gain (in terms of enzyme requirement) may thus be either a factor of 3 or a factor of 20 depending upon the criteria used in defining "reduction of viscosity".

Figure 6:
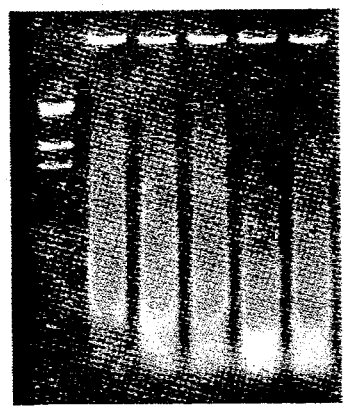
FIG. 6 shows the agarose gel electrophoretic pattern of non-digested nucleic acid present in the digest when the viscosity was usually estimated as "aqueous". Samples were taken from the digests shown in FIG. 5.

Samples taken from the lysates shown in FIG. 4, lines 2–6, when the "aqueous" state had just been reached, were subjected to agarose gel (1%) electrophoresis and subsequently stained with ethidium bromide. In all lanes, the stainable residual product constitutes a smear extending from a 21 kbp marker to the bromophenol blue band with decreasing amounts of slowly migrating material in the samples of higher nuclease concentration. This material comprises from less than 1 to a few percent of the nucleic acid present prior to the nuclease treatment (FIG. 6).

EXAMPLE 4

Elimination of residual nucleic acids

From gel electrophoretic analyses of limit digests of bacterial lysates, it was concluded that about 0.1% of the nucleic acids present in a lysate is not available for the action of the nuclease. It is suggested that the presence of residual nucleic acids is ascribable to protective masking of specific sequences, perhaps a membrane associated area of the genome, as only a minimal fraction of the total amount of nucleic acid remains after treatment with the nuclease.

In order to remove the residual nucleic acids, cell lysates were treated with the nuclease in the presence of various protein denaturing agents.

FTL lysates of 0.25 g of *E. coli* (wet weight) in a total volume of 0.6 ml were treated with 240 units of nuclease in the presence of 1–12M urea. The lysates were incubated at 30° C. for 1 hour or 18 hours. After incubation, 5 $\mu$l of the residue were analyzed by agarose gel electrophoresis and stained with ethidium bromide.

After 18 hours of digestion, a dramatically positive effect of 2–4M urea was observed, the presence of 4M urea in particular resulting in removal of all stainable material which has entered the gel.

FTL lysates of 0.68 g *E. coli* (wet weight) in a total volume of 2.5 ml TE were treated with $2.6 \times 10^3$ units of nuclease for 24 hours at 16° C. alone, in the presence of 0.1% SDS or 0.6% Triton ® X-100. Gel electrophoretic analyses indicated that residual nucleic acid could be digested by the nuclease if detergent was present.

From the results of these experiments, it appears that both types of detergents and protein denaturing agents make the residual, masked nucleic acids in a lysate available for the action of the nuclease.

EXAMPLE 5

Isolation of Serratia spp. A1

Bacteria were harvested from a rotten cucumber and plated out on DNase test agar. One colony showing a high level of exonuclease activity was further analyzed. Gram staining showed that it is gram negative. A preliminary identification indicated that the isolated organism is *Serratia liquefaciens*. However, until the classification is complete, it has tentatively been termed Serratia spp. A1 since there are many indications that it belongs to the Serratia group. The organism is resistant towards tetracylin and ampicillin, and it shows the same pattern of exoenzymes as the *Serratia marcescens*. (*Serratia liquefaciens* A1 was deposited in the DSM on May 8, 1985 under the Accession No. 3307.)

Preparation of chromosomal DNA from Serratia spp. A1

A culture of Serratia spp. A1 was grown overnight in LB medium and harvested by centrifugation (8,000 r.p.m. for 5 min.). The cells were washed twice in TEN-buffer (10 mM Tris, HCl, pH 8, 1 mM EDTA, 100 mM NaCl) and resuspended in 20 ml TEN-buffer containing 1 mg/ml lysozyme and 0.1 mg/ml RNase. The cells were incubated at 37° C. for 30 minutes and 20% SDS was added to a final concentration of 1%. After 60 minutes at a temperature of 37° C. (for total lysis), the lysate was incubated at 4° C. overnight. Next day the cell debris was removed by centrifugation (18,000 r.p.m. for 25 minutes). The supernatant was transferred to a new tube containing 2 ml 3M sodium acetate and 2 volumes of isopropanol. Upon gentle mixing, the DNA precipitated in threads which were picked up by means of a curved glass needle. The precipitated DNA was washed twice in 80% ethanol and resuspended in TEN-buffer. The DNA was further purified by buoyant density gradient centrifugation, and after appropriate dilution it was extracted with phenol and dialysed against TE-buffer (10 mM Tris-HCl, pH 8, 1 mM EDTA). Finally, the DNA was tested for absence of nuclease by incubation at 37° C. with restriction enzyme buffer.

Construction of a gene bank from Serratia spp. A1

The cloning vector plasmid pNU121 was used for the construction of a gene bank from Serratia spp. A1. The plasmid is described in Example 1.

pNU121 DNA with a unique EcoRI site in the $C_I$ gene was digested with the restriction enzyme EcoRI and mixed with Serratia spp. A1 DNA partially digested with EcoRI. The DNA was ligated at 15° C. overnight with T4 DNA ligase and transformed to $E.$ $coli$ strain MT102. Selection was made at 37° C. on LB plates containing 8 µg/ml tetracyclin, so that only cells harbouring pNU121 with inserted DNA will give rise to colonies. Approximately 8,000 colonies representing a gene bank of Serratia spp. A1 were isolated by this procedure.

Screening for lipase activity $E.$ $coli$ MT102 cells were transformed with the genomic bank of Serratia spp. A1 and cells carrying hybrid plasmids selected on LB plates with tetracyclin. Colonies were picked and transferred to microtiter dishes, each well containing A+B medium+1% casamino acids+thiamin and 200 mg/ml streptomycin and 8 µg/ml tetracyclin. Cells were grown overnight at 37° C. and replicas were made of the dishes. The substrate for the lipase enzyme, p-nitrophenylpalmitate was first suspended in isopropanol at a concentration of 6 mg/ml. 10 ml of the suspension was added to 90 ml 0.05M phosphate buffer pH 8.0 containing 207 mg of sodium deoxycholate. 0.5 ml of this solution was added to each well in the dishes. Yellow colour in a well indicates presence of lipase activity. One such clone was obtained. DNA was prepared and used to transform $E.$ $coli$ CSH50. Transformants were lipase positive. One such clone was isolated and DNA was prepared. The selected clone did not exhibit protease, phospholipase or nuclease activity.

The lipase-carrying plasmid pNU121-lip+

Plasmid DNA isolated from the lipase positive clone consisted of pNU121 with an inserted EcoRI fragment of approximately 8.4 Kb. The hybrid plamid is denoted pNU121-lip+. (Escherichia coli CSH50/pNU121-lip+ was deposited in the DSM on May 8, 1985 under the Accession No. 3313.).

Enzyme activities of lipase

The action of lipase activity on the substrate p-nitrophenylpalmitate can be followed spectophotometrically at $OD_{410}$. When both $E.$ $coli$/pNU121-lip+ and Serratia spp. A1 were grown exponentially in A+B medium+1% casamino acids and thiamin, the enzyme was shown to be present in the culture medium.

EXAMPLE 6

Preparation of chromosomal DNA from Serratia spp. A1

A culture of Serratia spp. A1 (vide Example 5) was grown overnight in LB medium and harvested by centrifugation (8,000 r.p.m. for 5 minutes). The cells were washed twice in TEN-buffer (10 mM Tris-HCl, pH 8, 1 mM EDTA, 100 mM NaCl) and resuspended in 20 ml TEN-buffer containing 1 mg/ml lysozyme and 0.1 mg/ml RNase. The cells were incubated at 37° C. for 30 minutes and 20% SDS was added to a final concentration of 1%. After 60 minutes at a temperature of 37° C. (for total lysis), the lysate was incubated at 4° C. overnight. Next day the cell debris was removed by centrifugation (18,000 r.p.m. for 25 minutes). The supernatant was transferred to a new tube containing 2 ml 3M sodium acetate and 2 volumes of isopropanol. Upon gentle mixing, the DNA precipitated in threads which were picked up by means of a curved glass needle. The precipitated DNA was washed twice in 80% ethanol and resuspended in TEN-buffer. The DNA was further purified by buoyant density gradient centrifugation, and after appropriate dilution it was extracted with phenol and dialysed against TE-buffer (10 mM Tris, HCl pH 8, 1 mM EDTA). Finally, the DNA was tested for absence of nuclease by incubation at 37° C. with restriction enzyme buffer.

Construction of a gene bank from Serratia spp. A1

The cloning vector plasmid, pNU121 (cf. Example 1), was used for the construction of a gene bank from Serratia spp. A1 (cf. Example 5).

pNU121 DNA with a unique EcoRI site in the $C_I$ gene was digested with the restriction enzyme EcoRI and mixed with Serratia spp. A1 DNA partially digested with EcoRI. The DNA was ligated at 15° C. overnight with T4 DNA ligase and transformed to $E.$ $coli$ strain MT102. Selection was made at 37° C. on LB plates containing 8 µg/ml tetracyclin, so that only cells harbouring pNU121 with inserted DNA gave rise to colonies. Approximately 8,000 colonies representing a gene bank of Serratia spp. A1 were isolated by this procedure.

Screening for phospholipase-positive clones $E.$ $coli$ MT102 cells were transformed with the genomic bank of Serratia spp. A1 and cells carrying hybrid plasmids selected on LB plates with tetracyclin colonies were replicated on egg yolk plates with tetracycline. A clearing zone around and a white precipitation on top of a colony indicates phospholipase activity. Fifteen such colonies were isolated, DNA was prepared and used to tranform CSH50. The phospholipase clone used was such a clone. The selected clone pNU121-phl+ exhibited only the phospholipase activity. (Escherichia coli MT102/pNU121-phl+ was deposited in the DSM on May 8, 1985 under the Accession No. 3311.)

The phospholipase carrying plasmids pNU121-phl+ and pOU57-phl+

Figure 8:
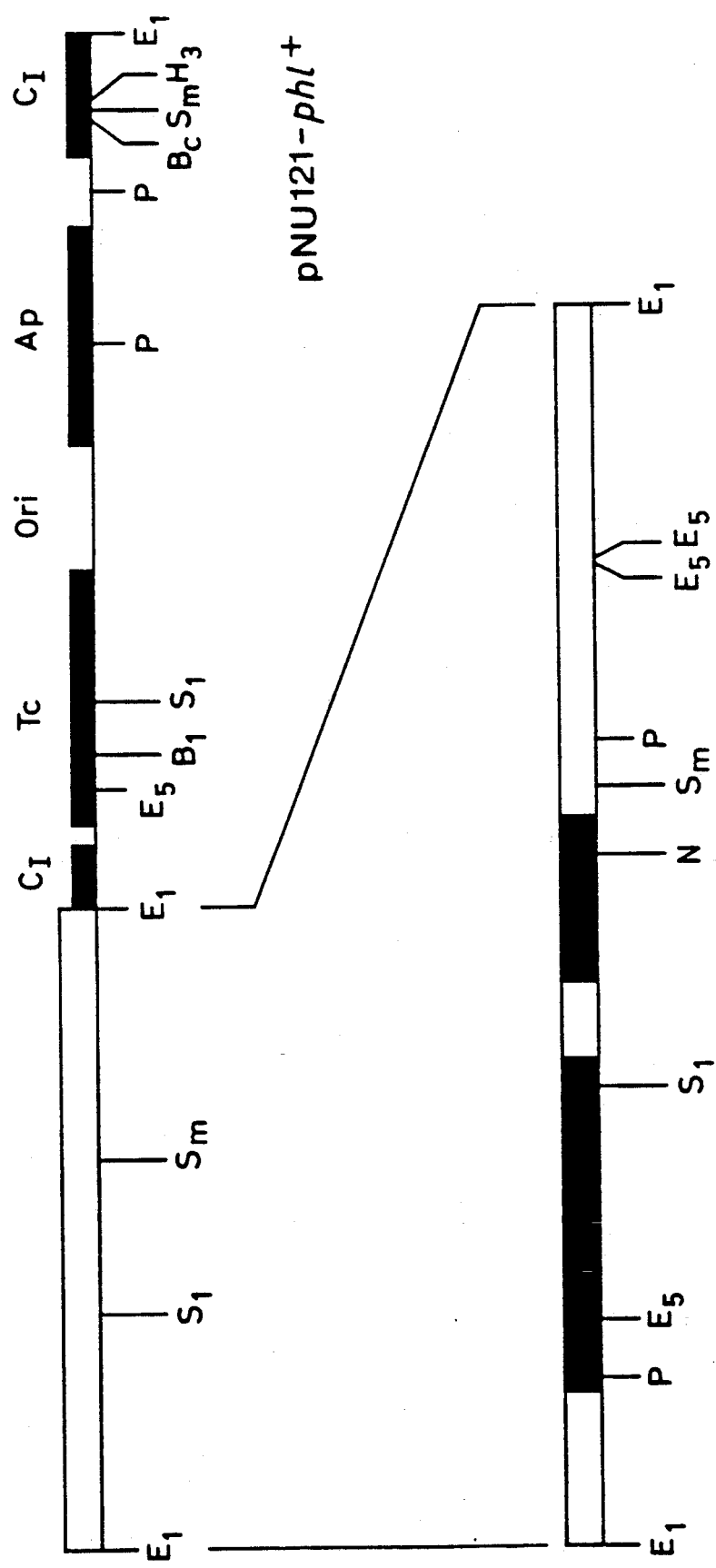
FIG. 8 shows a linear restriction enzyme and genetic map of the hybrid plasmid pNU121-phl+ consisting of the 4.5 Kb vector pNU121 and an insert of 3.2 Kb Serratia spp. A1 DNA containing the gene of the phospholipase operon. → indicates the promoter of the gene and the direction of transcription, ■ indicates a structural gene, Ap and Tc denote the genes for ampicillin and tetracycline resistance, respectively, C$_l$ denotes the λ repressor gene. Restriction enzymes: E$_1$=EcoRI, E$_5$=EcoRV, P=PstI, Sa=SalI, Sm=SmaI, N=NarI, H$_3$=HindIII, Bc=BclI, Ba=BamHI.

The plasmid DNA isolated from the phospholipase-producing clone, pNU121-phl+, consisted of pNU121 with a 3.2 Kb EcoRI fragment inserted in the $C_I$ gene (FIG. 8). This EcoRI fragment was cloned in the runaway plasmid pOU57. This runaway hybrid plasmid pOU57-phl+ conferred the phospholipase phenotype to other E. coli strains, and elevated expression of phospholipase was observed when present in Serratia strains. (Escherichia coli S17-1/pOU57-phl+ was deposited in the DSM on May 8, 1985 under the Accession No. 3312.) The phospholipase expression was amplified upon a temperature increase from 30° C. to 40° C. in the tested strains.

Enzyme activities of phospholipase

When E. coli cells containing the plasmid pNU121-phl+ were grown in A+B+1% casamino acids and thiamin, or LB, the phospholipase is only detected in the culture medium after the culture has reached a cell density corresponding to 0.7 $OD_{450}$ units. The viability of the E. coli strain was by no means affected by the presence of the plasmid.

The assay for phospholipase activity is based on reaction with egg yolk. Activity is assayed in 2% agarose gels containing egg yolk and chloramphenicol which inhibits growth of cells and protein synthesis in the gels.

Small wells were made in the gel into which 5 μl samples of supernatant (cells having been removed by centrifugation) of the growing culture were pipetted.

The enzyme reaction with the egg yolk produced a clearing zone in the turbid gel. Enzyme diffusion speed, i.e. $mm^2$ clearing zone per unit time, is used as a measure of enzyme activity. Measurements of phospholipase activity from growing cultures of E. coli/pNU121-phl+ and Serratia spp. A1 are shown in Table 7.

TABLE 7

| | Activities of Phospholipase | |
|---|---|---|
| Culture | Cell Density $OD_{450}$ | Extracellular Phospholipase Activity: $mm^2$/hour |
| MT102/pNU121-phl+ | 0.1 | 0 |
| | 0.5 | 0 |
| | 0.7 | 0.4 |
| | 0.9 | 0.7 |
| | 1.0 | 0.9 |
| | 1.3 | 1.3 |
| | 1.4 | 1.5 |
| | 1.5 | 1.8 |
| Serratia spp. A1 | 0.1 | 0 |
| | 0.5 | 0 |
| | 0.7 | 0.02 |
| | 0.9 | 0.10 |
| | 1.2 | 0.35 |
| | 1.8 | 0.90 |
| | 2.0 | 1.1 |

It appears that the E. coli culture secretes the enzyme to the culture medium more efficiently than Serratia. In both strains, the appearance of enzyme in the media is in the late exponential growth phase and continues into the stationary phase. Presence of 1% glucose in the media efficiently blocks synthesis of the enzyme in both hosts (not shown). A minor amount of detergent in the culture media (0.5% Tween® 80) has a stimulating effect on secretion (not shown).

DNA sequencing of the phospholipase clone

The 3.2 Kb EcoRI restriction fragment containing the phospholipase gene was sequenced using the "shotgun" cloning method of Messing et al. (Nucl. Acid Res. 9, 1981, p. 309) on the M13 phage derivatives Mp8 and Mp9 and the dideoxy chain termination technique of Sanger et al. (Proc. Natl. Acad. Sci. USA 74, 1981, p. 5463). In subcloning of the fragment, many different restriction enzymes were used: Sau3A, TaqI, AluI, RsaI, SalI, SmaI, PstI, EcoRI, PvuI, BssHII and EcoRV. The entire sequence was established by merging the collection of small (100–300 bases) pieces of DNA sequence. Most of the sequence has been determined for both strands.

Figure 9C:
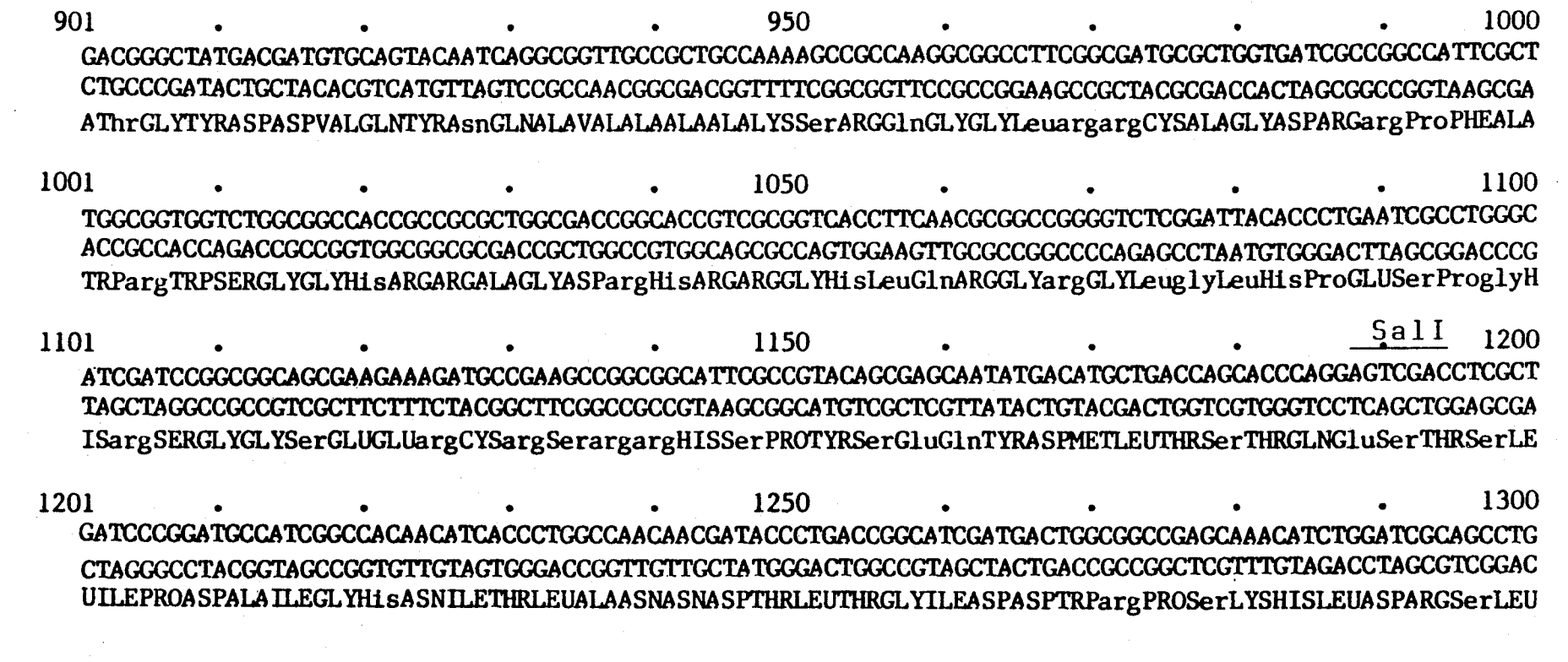

The sequence (FIG. 9) shows a major reading frame which starts from the left end of the fragment, at position 416, passing the SalI site to position 1372 where it ends.

Upstream of the frame is a Shine-Dalgarno homology (Shine, Dalgarno, Nature 254, 1975, p. 34) AAGGAG at position 405 immediately upstream of the ATG start codon. Upstream of the reading frame is a promoter region consisting of a −35 sequence CTGCC at position 351 and a −10 sequence TATTA at position 374. Upstream of the −35 sequence is a potential CAP-binding site from position 306 to 336.

The sequence indicates the presence of a gene which encodes a 319 amino acids protein with a predicted molecular weight of 34,056 daltons.

Insertion of the DNA fragment from position 0 to the PstI site at 441 upstream of the lac genes indicated the presence of a functional promoter in this DNA fragment. This promoter initiates lac expression at an $OD_{450}$ of 0.7 in a growing population of cells. Also this promoter was non-functional at any cell density in the presence of glucose, indicating catabolite repression probably mediated via the indicated CAP binding site.

By subcloning it has been verified that the necessary genetic information for the extracellular phospholipase activity is located within the 1.2 Kb fragment from position 360 to the FspI site at position 1551. It was also found that, in keeping with sequence information, it was necessary to clone this fragment in front of a promoter in order to obtain phospholipase activity in E. coli cells. In this way, orientation of the gene was also verified. The direction of transcription of the gene is from the left EcoRI site to the FspI site in keeping with sequence data. The promoter used was the temperature inducible system of c1857 and λpR. At 30° C. synthesis of phospholipase in E. coli cells was very low as judged from the normal plate assay. At temperatures above 37° C., there was a large production of enzyme. The gene product of this 1.2 Kb DNA fragment has been identified both in vivo and in vitro by incorporating radioactively labelled methionine. By SDS-polyacrylamide gel electrophoresis, the size of the gene product has been determined to 34 Kdalton, and it has been shown that in this gel system, phospholipase activity comigrates with the radioactively labelled 34 Kdalton protein.

We claim:

1. A method of producing an extracellular hydrolytic Serratia spp. enzyme selected from the group consisting of exocellular nuclease, exocellular phospholipase and exocellular lipase, comprising cultivating, E. coli in a culture medium, said E. coli harboring a hybrid plasmid which comprises DNA encoding an extracellular hydrolytic Serratia spp. enzyme selected from the group consisting of exocellular nuclease, exocellular phospholipase and exocellular lipase, operably linked to a promotor functional in said *E. coli*, under conditions conductive to the expression of said enzyme and its secretion into the culture medium, and harvesting the enzyme from the culture medium.

2. A method according to claim 1 wherein the Serratia spp. enzyme is a Serratia spp. nuclease.

3. A method according to claim 1 wherein the Serratia spp. enzyme is a Serratia spp. phospholipase.

4. The method of claim 1 wherein the hybrid plasmid is a plasmid with a conditionally uncontrolled replication behavior.

5. The method of claim 1 wherein the DNA sequence is

```
   1 GCCCCGCTGAAAGTCGTCTTGAAGGTGCTGCTGTCTTCGGTGGACAAGATAGTCAAAGTGCAGATCGCCAACAAGGTCGAGCAGGAAATCGCCCAGATCG
     CGGGGCGACTTTCAGCAGAACTTCCACGACGACAGAAGACACCTGTTCTATCAGTTTCCAGCTGCAGTTCCAGGTCGTCCTTTAGCGGGTCTAGC  100

101 AACAGCGGTGGTGCCGCCGCCGGCGGCGTCCGGTATCACCGGCGATCTGGCGCAGATGACGCATTACGTTCGCCGACACGGTCAACGACCTGCTGGATAATC
     TTGTCGCCACCACGGCGGCCGCCAGCCATAGTGGCCGCTAGACCGCTAGACCGCGTCTACTGCGTAATGCAAGCGGCTGTGCCAGTTGCTGGACGACTATTAG  200

201 CCCCCTTTGAAACGGCGTCTGTTGGACGGCTTTATTTCCGCCGCATTTCACGTGCGGCGTGGCTGTACCATGCCGACACATTCACACATGAATATGTT
     GGGGAAACTTTGCCGCAGACAACCTGCCGAAATAAAGGCGGCGTAAAGTGCACGCCGCACCGACATGGTACTGACTGTGTAAGTGTTGTACTTATACAA  300

301 GCATTGTTGTATTCGTTTCACTGCGATAAGTTTAATTTACTGTAAATATATACAGTACTTTTTTAACTTATTGAGGATATGAATATGCGCTTTAACAAC
     CGTAACAACATAAGCAAAGTGACGCTATTCAAATTAAATGACATTTATATGTCATGAAAAAAATTGAATAACTCCTATACTTATACGGAAATTGTTG  400

401 AAGATGTTGGCCTTGGTCGCCCTGCTGTTCGCCGCACAGGCGTCGGCCGACACGCTCGAATCCATCGACAACTGCGCGGTCGGCTGCCGACCGGCGGCA
     TTCTACAACCGGAACCAGCGGCGACGAGCTTAGGTAGCGTTGCGAGCTTAGGTTCAAGCGGTTGACCCACGAGCCGACGGCTGGCCGCCGT  500

501 TTCTCGTTGCACAGATAGCACGACGACAGTGCTTATACGTTGAACAACAGCACCAAGTTCGCCAACTGGGTGGCCCACCACCGAATAGTAGTGGTTTCTGTGTGG
     GCAGCAACGTGTCTATCGTGCGTCATGTCTTATACGTTGAACAACAGCACCAAGTTCGCCAACTGGGTGGCCCACCACCGAATAGTAGTGGTTTCTGTGTGG  600

601 GGCCAGCGGCAAGACGCGCAACTGAAAACCGATCCGGCGTGGCCTGCGCTGCGCCCTGTGCAACGGCGGCCGAGTTGGGCCGCTGGAATCCGCCGCGAAG
     CCGGTCGCCGTTCTGCGCGTTGACGACCAGCTGCTAGGCGCGACGACCAGCTCGAGCGCGGGGCACACGTTGAAGCGGTTGCAACCGCGGCCGCTCAAGC  700

701 GTCGATCGCGGTCATCAGGCGCGTCGCCTCGCTGGCCTCGGCCGCTGGGCGTCTCCAACATCACGCGCAAAAGTCCGATC
     CAGCTAGCGCCAGTAGTCCGCGGACCGGAGCGACCCGGCGACCGGAGCTGACCGCTTAATGGACAGTTGTAGTGCGGCGTTTTCAGGCTAG  800

801 TTAACCAGGGCGCCTGGGCGCTGAAGATCAGGAACGCAAGCTGATCGCGCCGATATCCTCGGTCTATACCGTGACCGGGCGCTGTATGA
     AATTGGTCCCGCGGACCCGCGACCAGCTCTTAGTCCTTGCGTTCGACTAGCGCGGATAGCTATAGGAGGACACTGGCCCGGCCGGCACTGGCACTGACATGACT  900

901 ACGGCGATATGGGCAAACTGCCGGGCGCACCCAGAAAGCGCACCATCCCAGCGCCTACTGGAAGGTGATTTTCATCAACAACAGCCCGGCGTGAACCAC
     TGCCGCTATACCCGTTTGACGCCCGTGGGTCTTTCGCGTGTGAGGGTCGGCGATGACCTTCCACTAAAGTAGTTGTTGTCGGGCCGCACTTGGTG  1000

1001 TATGCGCCTTTCCTGTTCGATCAGAACGCCGAAGGGCGGCGATTTCTGCCAATTCTTAAGGACGGTTAAGAGACGGTTAAGGCGCCACCTGCTCTAGCTCTTTGCCGCTGATCA
     ATACGGGCGAAAGGACAAGCTAGTCTTGTGCGGCTTCCCGCGGCTTAAGGACGTTCCACCTGCTCTAGCTCTTTGCTGCCGGCCGGCGGAGTCCGGTGGTG  1100
```

-continued

1101 TCTGGGCCGGTCTGCCGGACGACGTGCAGGCTTCGCTGAAGAGCAAACGGCGTCCTGCCGGAGTTGATGGGCTGCAAAAACTGACGAAAACCGCCGAAG 1200
     AGACCCGGCCAGACGGCCTGCTGCACGTTCTCGTTCGAAGCGACTTCCGCGCCAGGACGGCCTCAACTACCGACGTTTTGACTGCTTTTGGCGGCTTC

1201 CGGGTTTATTTTTCACGCGGGCGGCGGCGGATTATCCCGTCGCGCCTTTTGCGCGGCGGCCAACTCACGCTGACGGGGTGAGGCTACCGGGGCC 1294
     GCCCAAATAAAAGTGCGCCCGGCCGCCGCCTAATAGGGCAGCGCGGAAAACGCGCCCGCCGGTTGAGTGCGACTGCCCCACTCCGATGGCCCCGG

6. A method according to claim 1 of producing the enzyme substantially free from other bacterial protein, in which the enzyme is secreted from the *E. coli* into the culture medium and is harvested from the culture medium.

7. The method of claim 1 wherein the DNA encodes a Serratia spp. nuclease which, prior to removal of the amino-terminal signal peptide, has the amino acid sequence MetArgPheAsnAsnLysMetLeuAlaLeuValAlaLeuLeuPheAlaAlaGlnAlaSerAlaAsp
ThrLeuGluSerILeAspAsnCysAlaValGlycysProThrGlyGlySerSerAsnValSerIleValArg
HisAlaTyrThrLeuAsnAsnAsnSerThrThrLysPheAlaAsnTrpValAlaTyrHisIleThrLysAsp
ThrProAlaSerGlyLysThrArgAsnTrpLysThrAspProAlaLeuAsnProAlaAspThrLeuAlaProAla
AspTyrThrGlyAlaAsnAlaAlaLeuLysValAspArgGlyHisGlnAlaProLeuAlaSerLeuAlaGly
ValSerAspTrpGluSerLeuAsnTyrLeuSerAsnIleThrProGlnLysSerAspLeuAsnGlnGlyAla
TrpAlaArgLeuGluAspGlnGluArgLysLeuIleAspArgAlaAspIleSerSerValTyrThrValThr
GlyProLeuTyrGluArgAspMetGlyLysLeuProGlyThrGlnLysAlaHisThrIleProSerAlaTyr
TrpLysValIlePheIleAsnAsnSerProAlaValAsnHisTyrAlaAlaPheLeuPheAspGlnAsnThr
ProLysGlyAlaAspPheCysGlnPheArgValThrValAspGluIleGluLysArgThrGlyLeuIleIle TrpAlaGlyLeuProAspAspValGlnAlaSerLeuLysSerLysProAlaSerCysArgSer |.

8. The method of claim 1 wherein the DNA encodes a Serratia spp. phospholipase encoded by the DNA sequence

```
ATGAGTATGCCTTTAAGTTTTACCTCTGCAGTATCCCCGGTGGCCGCGATCCCTACGCCTCGCGCCTGCCGAGACGCGGACGG
TACTCATACGGAAATTCAAAATGGAGACGTCATAGGGGCCACCGGGCGCTAGGGATGCCGAGCGCGGCGACGGCTCTGCGCCTGCC

CGGCGAGCCTGCGGCACGCCGCAAATCCGGGCCGGTGGCCTGGCCTCTCCCTCTCAGAACGCTGAAGCGCAGAATCTGTTGAATAC
GCCGCTCGGACGCCGTGCGGGCCGTTTAGGCCCGGCCACCGAGGGGAGTCTTGTGCGACTTGCGCGTCTTAGACAACTTATG

GCTGGTCGGCGATATCTCAGCGGCGGCACCGGCGGCGCGCCGGCGTGACGCGGGGCAGCAATCGCAGGAGGGGAT
CGACCAGCCGTATAGAGTCGCCGCCGTGCCGCCTGCCTGCGCCGCCCGACTGCGCCGCCCGTCGTTAGCGTCCTCCCCCTA

TATGCGTTGGCGCTGTTGTGGCCAAGGACGTTTACTCACTCAATGAGTGAGTTACCGGTTCAACCGCCTGAGCGACACCGCTG
ATACGCAACCGGACAACCGGTTCCTGCAAATGAGTTACCGGTTACCGGTTCAACCGCCCAAGTTGGGGACTCGCTGTGGCGAC

CTCGGTTTCGGCATCGATCCCGCCAGCTGCGACGACGGCAGCGGTTCCAGGCTGGATTTACAGCAACGACAAACAGTAT
GAGCCAAAGCCGTAGCCGTCGGACGTGCTGCGCCCTGCGCCAAAGGGTCCGACCCTAAATGTCGTTGCTGTTTGTCATA

GTGTTGGGCGTTCGCGGCACCAACGACTGCCGCCGATTGGCTGGCGCAGCAACGTGCGGCGACGGGCTGGTCAGTAC
CACAACCGCAAGCGGCCGTGGTTGCTGACCGGCGTTTCGACCGGAACCGGTCGCGTTGCAGCGCGATACTGCTACACGTCATG

AATCAGGCGGTTGCCGCTGCCAAAAGCCGCCAGCGGACCGGCCTGGGCCCACCGTCACCTTCAACGCGGCCGGGTCTCGATTACACCCTGAATCGCCT
TTAGTCCGCCAACGGACGGTTTCGACCGGTTTCGCGGTTCCGCCGGGTTCCGCCGGGTTGCGCCGGTCAGTGGAAGTTGCGCCGGCAGTGGAAGCTTAATGCTGGGACTTAGCGGA

CTGGCGGCCACCGCCGCCGGCCTGGGACGCCAGCGGACCGCGGCCGGGGCATTCGCCGTACAGCGAGCAATATGACATGCTGACCAGCA
GACCGCGGGTGGCGGCGACCGGCCCGGCCTGGCCGTGCAGCGCCAGCCCCAGAGCCTAATGGCGTACTGTATACGTGACTGGTCGT

GGGCATCGATCCGGCGGCAGCGGCGAAGAAAGATGCCGAAGCCGGCTTCGGCCGTACAGCGCATGCGCTCGTTAAGCGGCATGTCGCTATCTGTATACGTGAC
CCCGTAGCTAGGCCGCCGCCCGCTGCTTCTTTCTACGGCTTCGGCCGCCGTAAGCGGCATGCGCTCGTTATACTGTATCGACTGGTCGT

CCCAGGAGTCGACCTCGCTGATCCCGGATGCCATCGCCACAACATCACCCTGGCCAACGATACCCTGGACGGCATCGATGA
GGGTCCTCAGCTGGAGCGACTAGGGCCTACGGTGTAGCGGCCTATGGGGACCGGTTGTTGCTATGGGACTGGCCGTAGCTACT

CTGGCGGCCGAGCAAACATCTGGATCGCAGCCTGACGGCCACGGCATCGACAAGGTGATAAGCTCGACAAGTGAACAAAGCCG
GACCGCCGGCTCGTTTGTAGACCTAGCTCGGACTGCGTAGCTGTTCCACTATTCGAGCTACGGCTACGGCTACCGCCTTGTTTCGGC

TGGGAGGCGAAGGCCAATGCCTGA
ACCCTCCGCTTCCGGTTACGGACT.
```

9. A DNA fragment comprising a DNA sequence encoding a Serratia spp. phospholipase.

10. A DNA fragment according to claim 9 wherein the DNA sequence is 5,173,418

```
                                                            250                                                             300
201  GTTATCGCCCCGCACCTTTACCGAAATGGCTGTAATTTGCGGGCGCAGTCAATCAGGAGCTTCGGCTGCCTCCCTTTCTGGCGTTTGGCGGCCGAAAACCGAACGTG
     CAATAGCGGGGCGTGGAAATGGCTTTCGGACATTAAACGCCCGCCAGTCAGTTAGTCCTCGAAGCCGAGGGAAAGACCGCAAACCGCCGGCTTTGGCTTGCAC
                                CAP-SITE     PROMOTER AREA.
                                                            330                                                             400
301  GATCACATTCTGTACAAAGATAAGCATTCTAATACAGAACTCATCCGACCTGACTTAGTCTTGAGTAGGCTGGATCGGATAAATCAGCACCTATTTAGGTGCTCAATAAAAAGTCTAT
     CTAGTGTAAGACATGTTTCTATTCGTAAAGATTATGTCTTGAGTAGGCTGGATCGGATAAATCAGCACCTATTTAGGTGCTCAT AAATCCACGAGTTATTTTTCAGATA
          S.D.       phl-gene
                                                            450                                                             500
                                                                                                    PstI
401  CGACAAGGAGTCGGACATGAGTAGTGCCTTTAAGTTTTACCTCTGCAGTATCCCCCGGTGGCCGCGATCCCGCGCTCCGCCGCTGCCGAGACGCGGACGG
     GCTGTTCCTCAGCAGTCACATGCTACTCATTCGGAAATTCAAATGGAGAGCGTCATAGGGGCCACCGGCGCTAGGATGCGCGAGGCGGCGACGGCTCTGCGCCTGCC
        fMET Ser MET Pro Leu Ser PHE THR SER ALA VAL SER Pro VAL ALA ALA ILE Pro Thr Pro ARG ALA ALA ALA ALA Glu Thr arg Thr A
                                                                                           EcoRV
                                                            550                                                             700
501  CGGCGAGCCTGCGGCACGCCGGCAAATCCGGCCGGTGGCCTCTCCCTCTCAGAAACGCGCAGAATCTGTGAATACGCTGGTCTGGTCGGCGATAT
     GCCGCTCGCGGTCGGACGCCGTTTAGGCCGGCCGGTTCAATCAAATGGCGTCTTGCGCGTCTTAGACAACTTATGCGACCAGCCGCTATA
      LA ALA Ser LEU arg His ALA GLY LYS SER gly   PRO VAL ALA SER Pro SER GLN ASN Thr  LEU ASN ALA GLN Asn LEU Val GLY ASP IL
                                                            650                                                             700
601  CTCAGGCGGCGGCACCGACGGCGGCAGCGCCGGGCGTGACGCGGCAGCAATCGCAGGAGGGGATTATGCGTTGGCGTTGTTGGCCAAGGACGTT
     GAGTCGCCGCCGTGGCTGCCGCCGTCGCGGCCCGCACTGCGCCGTCGTTAGCTCCTCCCCCTAATACGCAACCGGTTCCTGCAA
      ESer ALA ALA ALA ALA PRO GLY VAL Thr arg gly GLN Gln Ser GLN gly ASP TYR ALA Leu ALA LEU ALA Lys ASP Val
                                                            750                                                             800
701  TACTCACTCAATGGCCAGGCGCCCGGTTCAACCGCTGAGCGACAGCGCGCTGTTTCGGCATGCATCGATCCCGCAGCTGCTCGACGACGGGCA
     ATGAGTGAGTTACCGGTCCCGGCGGGCCAAGTTGGCGACTCGCTGTCGCGCAATAGCCGTAGGCGGTCGGACGTGCTGCCCGT
       TYR Ser  Leu Asn GLY GLN GLY ALA ALA gly   PHE ASN ARG LEU Ser ASP Ser   ALA LEU Leu GLY PHE GLY ILE   GLY LEU ASP Pro ALA Ser   LEU HIS   ASP ALA GLY LYS S
                                                            850                                                             900
801  GCGGTTTCCAGGCTGGGATTTACAGCAACGACAAACAGTATGTGTTCGCCGGCACCACCGGTGTTGCTGACCGCTGTAACGACTGGCGGTGACGCTCCG
     CGCCAAAGGTCCGACCCTAAATGCTTGCTGTTTGTCATACACAAGCGGCCGTGGTGGCCACAACGACTGGCGACATTGCTGACCGCCACTGCGCAGGC
       er GLY PHE GLN ALA gly ILE TYR Ser  ASN ASP LYS GLN TYR VAL Leu   ALA PHE ALA GLY THR THR ASP TRP ARG ASP TRP LEU ASP   ASN VAL arg  GLN ALA L
                                                            950                                                            1000
901  GACGGGCTATGACGATGTGCAGTACAATCAGGCGGTTGCCGCTGCCAAAGCCGCCAAGGCGGCCCTTCGGCAGCCGCTTCCGGCGACCACTAGCGCCGGTAAGCGA
     CTGCCCGATACTGCTACACGTCATGTTAGTCCGCCAACGGCGACGGTTTCGGCCGGTTTCGGCGGAAGCCGTCGGCCGAAGCCGTCGGCGGCCATTGGCCGGCCATTCGCT
        A Thr GLY TYR ASP ASP VAL GLN TYR Asn  GLN ALA VAL ALA VAL ALA ALA ALA LYS Ser   ARG Gln GLY GLY Leu  arg   CYS ALA GLY ASP ARG arg   Pro PHE ALA
                                                           1050                                                            1100
1001 TGGCGGTGGTCTGGGCCACCGGCGCCGGGGTCTCACCTTCAACGCGGCGGGCCGGTCTCGGAATCGCCTGGGC
     ACCGGCCACCAGACCCGGTGGCCGCGGCCCCAGAGGTGAAGTTGCGCCGGCCAGCTAACCTAAGTCGAACCCGA
       TRP arg   TRP SER GLY GLY His   ARG ARG ALA GLY arg   His   ARG ARG GLY Leu   His   Leu Gln ARG GLY Leu   gly   ARG GLY Leu  gly   Leu His   Pro GLU Ser Pro gly  H
```

-continued

```
                                                                   SalI
1101                      1150                              1200
ATCGATCCGGCGGCAGCGAAGAAAGATGCCGAAGCCGGCATTCGCCGTACAGCGAGCAATATGACATGCTGACCAGCACCCAGGAGTCGACCTGCT
TAGCTAGGCCGCCGTCGCTTCTTTCTACGGCTTCGGCCGTAAGCGGCATGTCGCTCGTTATACTGTACGACTGGTCGTGGGTCCTCAGCTGGAGCGA
IS arg  SER GLY GLY Ser GLU GLU arg CYS arg  arg Ser arg HIS Ser PRO TYR ASP  TYR ASP MET LEU THR Ser THR GLN Glu Ser THR Ser LE 1201                      1250                              1300
GATCCCGGATGCCATCGGCCACACAACATCACCCTGGCCAACAACGATACCCTGACCGGCATCGATGACTGACTGACCGCCGAGCAAACATCTGGATCGCAGCCTG
CTAGGGCCTACGGTAGCCGGTGTTGTAGTGGGACCGGTTGTTGCTATGGGACCGGCCGTAGCTACTGACTGACGGCTCGTTTGTAGACCTAGCGTCGGAC
UILE PRO ASP ALA ILE GLY His ASN ILE THR LEU ALA ASN ASP THR LEU THR ASP ASP  PRO Ser  LYS HIS LEU ASP ARG Ser LEU 1301                      1350  phl-stop                      1400
ACGGCGCACGGCATGACAAGGTGATAAGCTCGATGGCGGAACAAAAGCCGTGGGGACGGAAGGCCAATGCCTGAAGGGCGTCGCTTGCGGGGGCGCTG
TGCCGCGTGCCGTACTGTTCCACTATTCGAGCTACCGCCCTTGTTTTCGGCACCCTTGTTTCCGCTTCCGCAAGGCGAACGCCGCCCCGCGAC
Thr ALA His GLY ILE ASP Lys VAL ile Ser Ser MET ALA GLU Gln Lys PRO TRP Glu ALA Lys ALA Asn ALA 1401                      1450                              1500
GCGATAGCCTTACTGGGCTGGTCGCGGTGACCGGTGGCCACTGGCCAAATGACTACTACCGATTCCTCGTTGTCTACCCCGTCCTAAAGCGGCAAACTGCCGGTGTCGC
CGCTATCGGAATGACCCGACCAGCGCCACTGGCCGTTACTGATGATGGCTAAGGAGCAACAGATGGGGCAGGAGATTTCGCCGTTTGACGGCCACAGCG
GCTATCGGAATGACCGCGACCAGCGCCACTGGCCGTTACTGATGATGGCTAAGGAGCAACAGATGGGGCAGGAGATTTCGCCGTTTGACGGCCACAGCG 1501                1550 FspI                              1600
AATCTGGGCTGGCTCAGGCGGTGGCGCGACCGGTGCCGGCACCGGTGCGCGTGGCGCGTGGCGATACCGGCAGGCCACGCAGGATCCATGCGCAAGGGCGATCGGCAGGTCA
TTAGACCCGACCGAGTCCGCCACCGCGCTGGCCACGGCCGTGGCCACGCGCACCGCGCACCGCTATGGCCGTCCCATAGGTACGCGTTCCGGTGCGTCCTAGCGGCGCTTGCGCGAACGGGCGCTTGCCCCGCTAGCCGTCCAGT.
```

* * * * *